(12) United States Patent
Gounder et al.

(10) Patent No.: US 12,679,788 B2
(45) Date of Patent: Jul. 14, 2026

(54) STABLE PRODUCT OLIGOMER SELECTIVITY FROM OLEFIN OLIGOMERIZATION ON ZSM-5 ZEOLITES AND ZEOTYPES

(71) Applicant: PURDUE RESEARCH FOUNDATION, West Lafayette, IN (US)

(72) Inventors: Rajamani P. Gounder, West Lafayette, IN (US); Elizabeth E. Rogers, Dresser, WI (US); Songhyun Lee, West Lafayette, IN (US); Evan Sowinski, West Lafayette, IN (US)

(73) Assignee: PURDUE RESEARCH FOUNDATION, West Lafayette (IN)

( * ) Notice: Subject to any disclaimer, the term of this patent is extended or adjusted under 35 U.S.C. 154(b) by 147 days.

(21) Appl. No.: 18/440,016

(22) Filed: Feb. 13, 2024

(65) Prior Publication Data

US 2024/0270664 A1 Aug. 15, 2024

Related U.S. Application Data

(60) Provisional application No. 63/445,206, filed on Feb. 13, 2023.

(51) Int. Cl.
| | |
|---|---|
| *C07C 2/12* | (2006.01) |
| *B01J 29/40* | (2006.01) |
| *B01J 35/77* | (2024.01) |
| *B01J 37/30* | (2006.01) |

(52) U.S. Cl.
CPC ................. *C07C 2/12* (2013.01); *B01J 29/40* (2013.01); *B01J 35/77* (2024.01); *B01J 37/30* (2013.01); *C07C 2529/40* (2013.01)

(58) Field of Classification Search
CPC ........ C07C 2529/40; C07C 2/12; B01J 29/40; B01J 35/77; B01J 37/30
See application file for complete search history.

(56) References Cited

U.S. PATENT DOCUMENTS

| | | | | |
|---|---|---|---|---|
| 9,789,476 | B2 * | 10/2017 | Takamitsu | ............... B01J 29/70 |
| 2006/0199987 | A1 * | 9/2006 | Kuechler | ............... C10G 50/00 |
| | | | | 585/502 |
| 2010/0312031 | A1 | 12/2010 | Heidemann | |
| 2013/0053609 | A1 | 2/2013 | Burgfels | |
| 2016/0176777 | A1 * | 6/2016 | Yao | ......................... B01J 35/643 |
| | | | | 585/533 |
| 2022/0064012 | A1 | 3/2022 | Gounder | |

OTHER PUBLICATIONS

Kim et al. ("Spatial distribution, strength, and dealumination behavior of acid sites in nanocrystalline MFI zeolites and their catalytic consequences", Journal of Catalysis 288, 2012, p. 115-123) . (Year: 2012).*
International Search Report and Written Opinion for PCT/US2024/15492 dated May 14, 2024.

* cited by examiner

*Primary Examiner* — Ali Z Fadhel
(74) *Attorney, Agent, or Firm* — Edmonds & Omaidalka, P.C.

(57) ABSTRACT

MFI zeolite and methods for converting alkenes to higher liquid products. The method includes contacting one or more alkenes having about 2 to about 12 carbon atoms with a MFI zeolite having a silicon to aluminum ratio (Si:Al) of about 20 to about 100 and a crystallite size of about 0.001 μm to about 0.1 μm; and oligomerizing the one or more alkenes in the presence of the MFI zeolite to form an oligomer having 4 to 26 carbon atoms.

17 Claims, 28 Drawing Sheets

| CBV2314 | EB6-053 | SL1-070 |
|---|---|---|

STABLE PRODUCT OLIGOMER SELECTIVITY FROM OLEFIN OLIGOMERIZATION ON ZSM-5 ZEOLITES AND ZEOTYPES

GOVERNMENT LICENSE RIGHTS

This invention was made with government support under Cooperative Agreement No. EEC-1647722 awarded by the National Science Foundation. The government has certain rights in the invention.

BACKGROUND

Field of the Invention

Embodiments provided herein relate to MFI zeolites and zeotypes. More particularly, embodiments provided herein relate to MFI (ZSM-5) zeolites and zeotypes for olefin oligomerization.

Description of the Related Art

Light alkene oligomerization is a promising pathway to synthesize higher molecular weight hydrocarbons for transportation fuels and additives. Solid acids including supported phosphoric acid, acid resins, amorphous silica-alumina, and zeolites have been used in industrial oligomerization processes, with MFI zeolites garnering the most attention for these reactions due to its resistance to coke formation and high selectivity to linear olefins. MFI zeolites in their aluminosilicate composition are also known as ZSM-5. ZSM-5 is used in the Mobil Olefins to Gasoline and Distillate (MOGD) process, and there are several patents from the 1980s associated with this process.

Zeolites contain tetrahedral silicon atoms linked by oxygen, forming charge-neutral crystalline structures. The isomorphous substitution of trivalent aluminum atoms for tetravalent silicon introduces a negative charge imbalance that can be compensated by protons, which act as Brønsted acid sites for catalysis. Zeolites can also be synthesized with varying crystallite sizes and morphologies, with smaller crystallites leading to shorter diffusion pathlengths. Zeotypes are zeolite-like materials that include other elements in addition to silicon, aluminum, and oxygen.

Oligomerization is also accompanied by the undesired cracking (β-scission) reaction to form smaller hydrocarbons from oligomers. High selectivity is therefore achieved by preferentially slowing cracking reactions relative to oligomerization. Other synthetic variables that may affect the product distribution of olefin oligomerization in MFI include local aluminum proximity and the interplay between crystal size and bulk aluminum content. Another important consideration is how oligomerization rate and product selectivity change with time-on-stream. Generally, reaction rates decrease with time on-stream due to catalyst deactivation, which results from the build-up of heavier hydrocarbons within zeolite pores that introduce diffusion limitations and also from other mechanisms of deactivation such as active site poisoning or pore blocking. Additionally, product selectivities are observed to change with time-on-stream as zeolites deactivate, generally shifting the distribution towards primary products in the reaction network, such as hexene dimer products.

There is still a need, therefore, for new catalysts and catalyst synthesis approaches that can lead to more stable time-on-stream operation, in terms of both the reaction rate and product selectivity.

SUMMARY

MFI zeolites and method for using same to convert one or more alkenes to higher liquid products are provided. The MFI zeolite can have a silicon to aluminum ratio (Si:Al) of about 10 to about 100 and a crystallite size of about 0.001 $\mu$m to about 0.1 $\mu$m. In at least one embodiment, the method includes contacting one or more alkenes having 2 to 12 carbon atoms with a MFI zeolite having a silicon to aluminum ratio (Si:Al) of about 20 to about 100 and a crystallite size of about 0.001 $\mu$m to about 0.1 $\mu$m; and oligomerizing the one or more alkenes in the presence of the MFI zeolite to form an oligomer having 4 to 26 carbon atoms.

In at least one other embodiment, a method for making a MFI zeolite is provided. One particular method for making the MFI zeolite can include: combining a source of quaternary ammonium surfactant with hydrocarbon chains, a source of sodium, and water to form an aqueous solution; homogenizing the aqueous solution; adding a source of aluminum to the homogenized aqueous solution to form an intermediate agent; homogenizing the intermediate agent to form an aluminum-containing intermediate agent; adding a source of silicon to the aluminum-containing intermediate agent to form an aluminosilicate-containing intermediate agent; homogenizing the aluminosilicate-containing intermediate agent to form a synthesis gel; crystallizing the synthesis gel to form crystallized MFI zeolite solids; and then recovering the crystallized MFI zeolite solids.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are, therefore, not to be considered limiting of its scope, for the invention may admit to other equally effective embodiments. It is emphasized that the figures are not necessarily to scale and certain features and certain views of the figures can be shown exaggerated in scale or in schematic for clarity and/or conciseness.

260° C., propene partial pressure 165 kPa, space velocity 0.1 (mol $C_3H_6$) (mol $H^+$)$^{-1}$ s$^{-1}$ and MFI CATALYST 1/EB6-053 using reaction condition: 260° C., propene partial pressure 165 kPa, space velocity 0.2 (mol $C_3H_6$) (mol $H^+$)$^{-1}$ s$^{-1}$.

Figure 5:
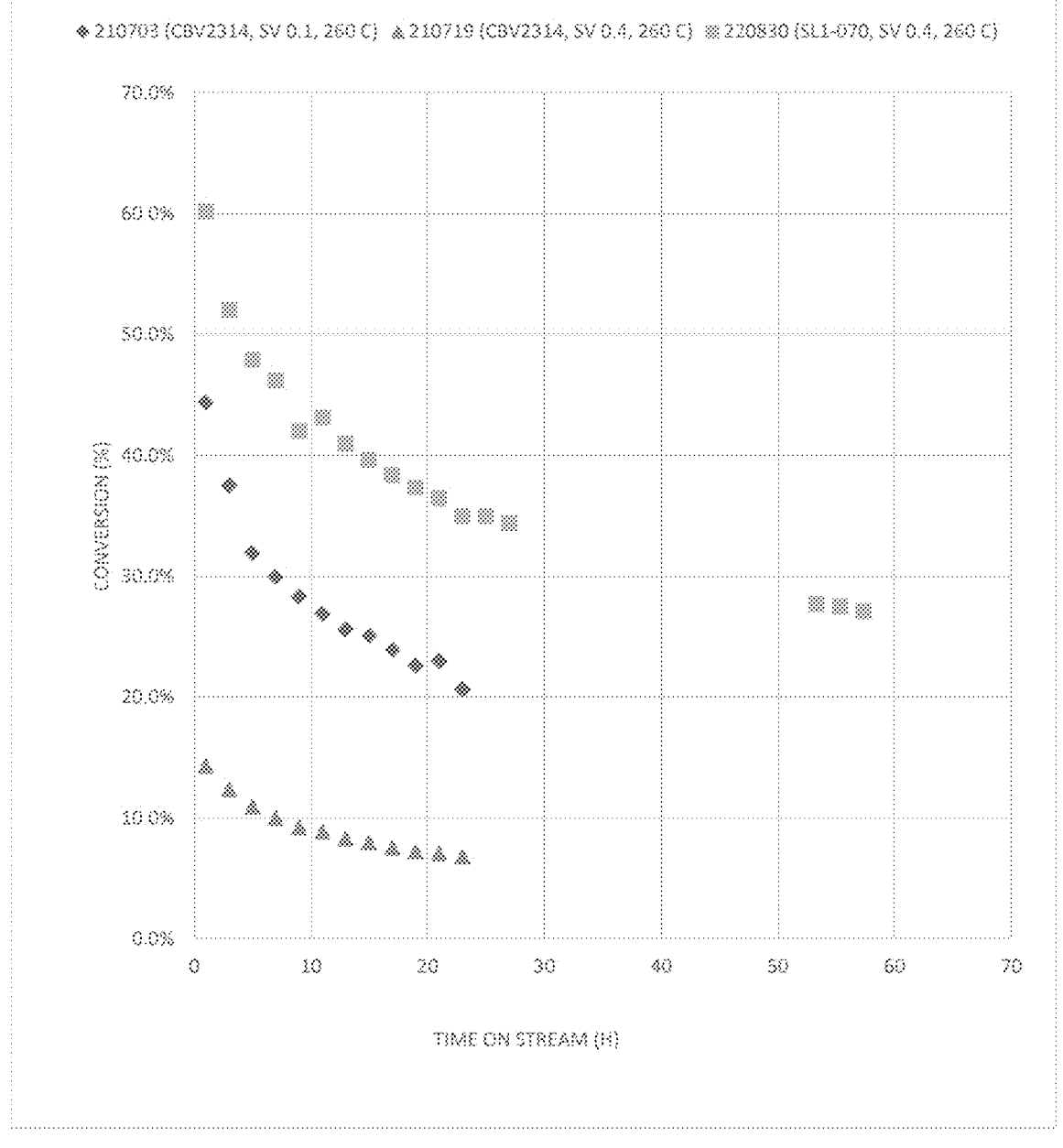

FIG. 5 depicts time-on-stream conversion of propene oligomerization on CBV2314 and MFI CATALYST 2/SL1-070 using reaction conditions: 260° C., propene partial pressure 165 kPa, space velocities of 0.1 and 0.4 (mol $C_3H_6$) (mol $H^+$)$^{-1}$ s$^{-1}$.

Figure 6A:
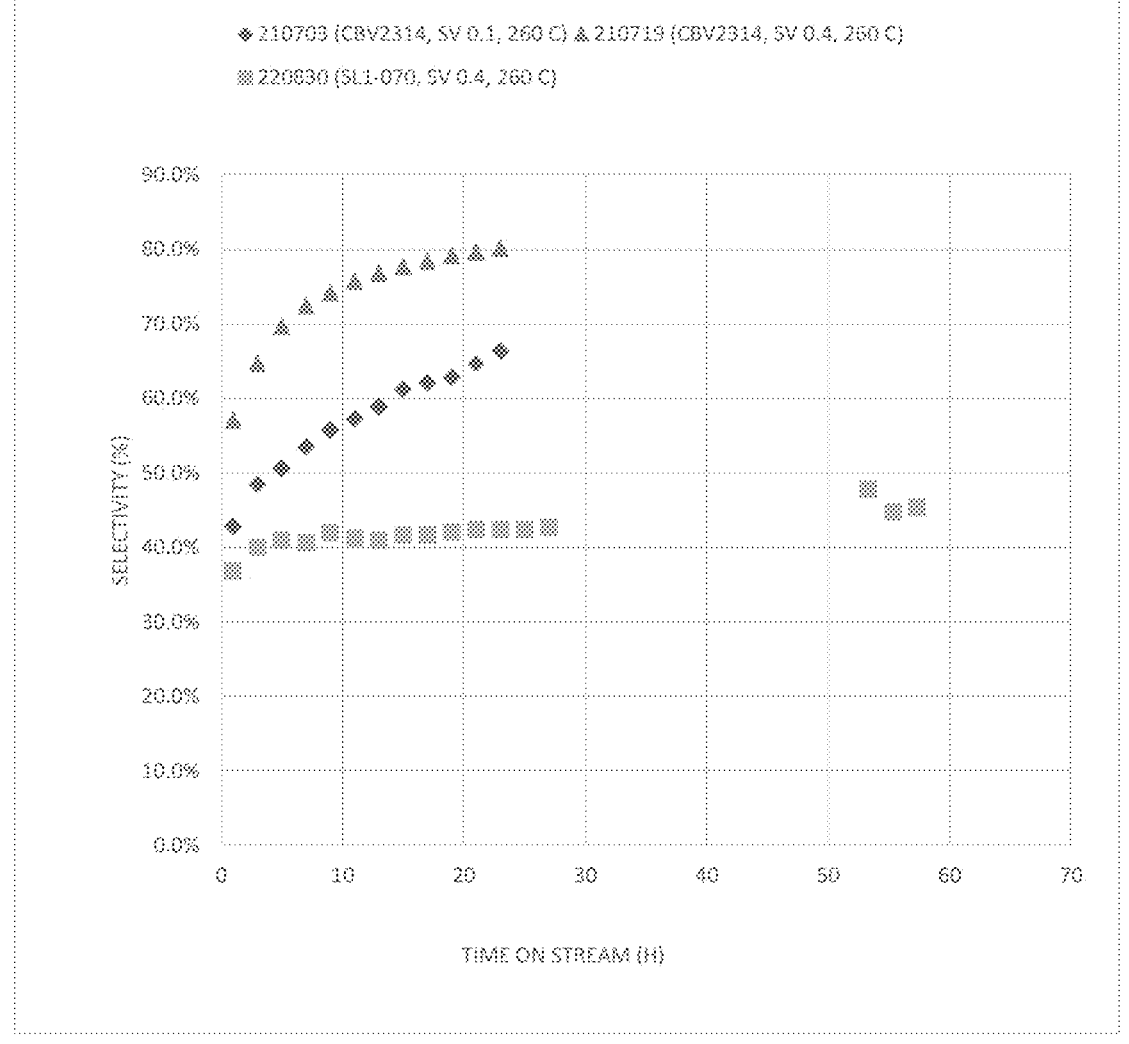
Figure 6B:
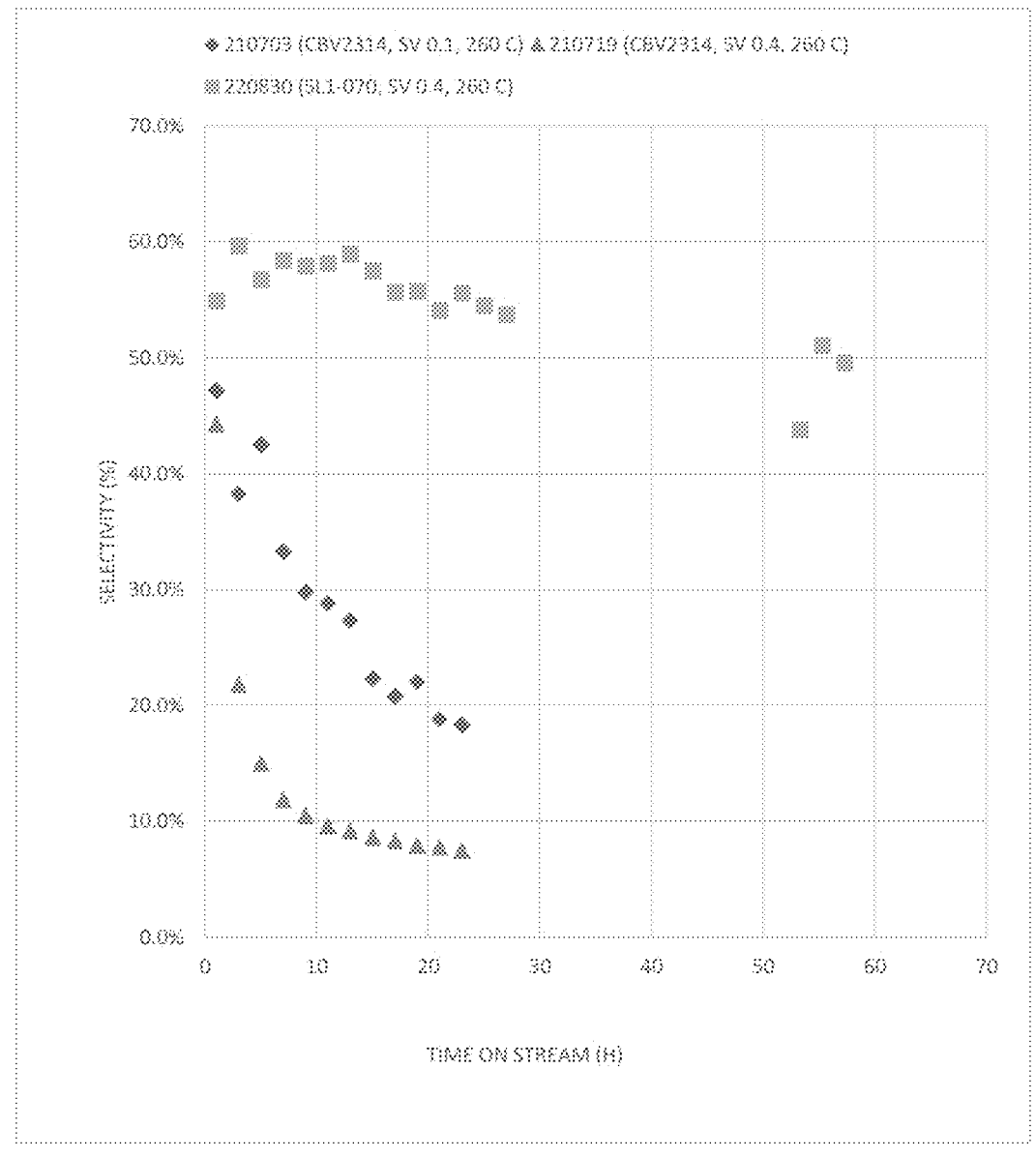

FIG. 6A and FIG. 6B depict time-on-stream selectivity to primary oligomerization products ($C_6$, $C_9$, $C_{12}$, $C_{15}$) and oligomers with carbon number >10 ($C_{10+}$) for CBV2314 and MFI CATALYST 2/SL1-070.

Figure 7:
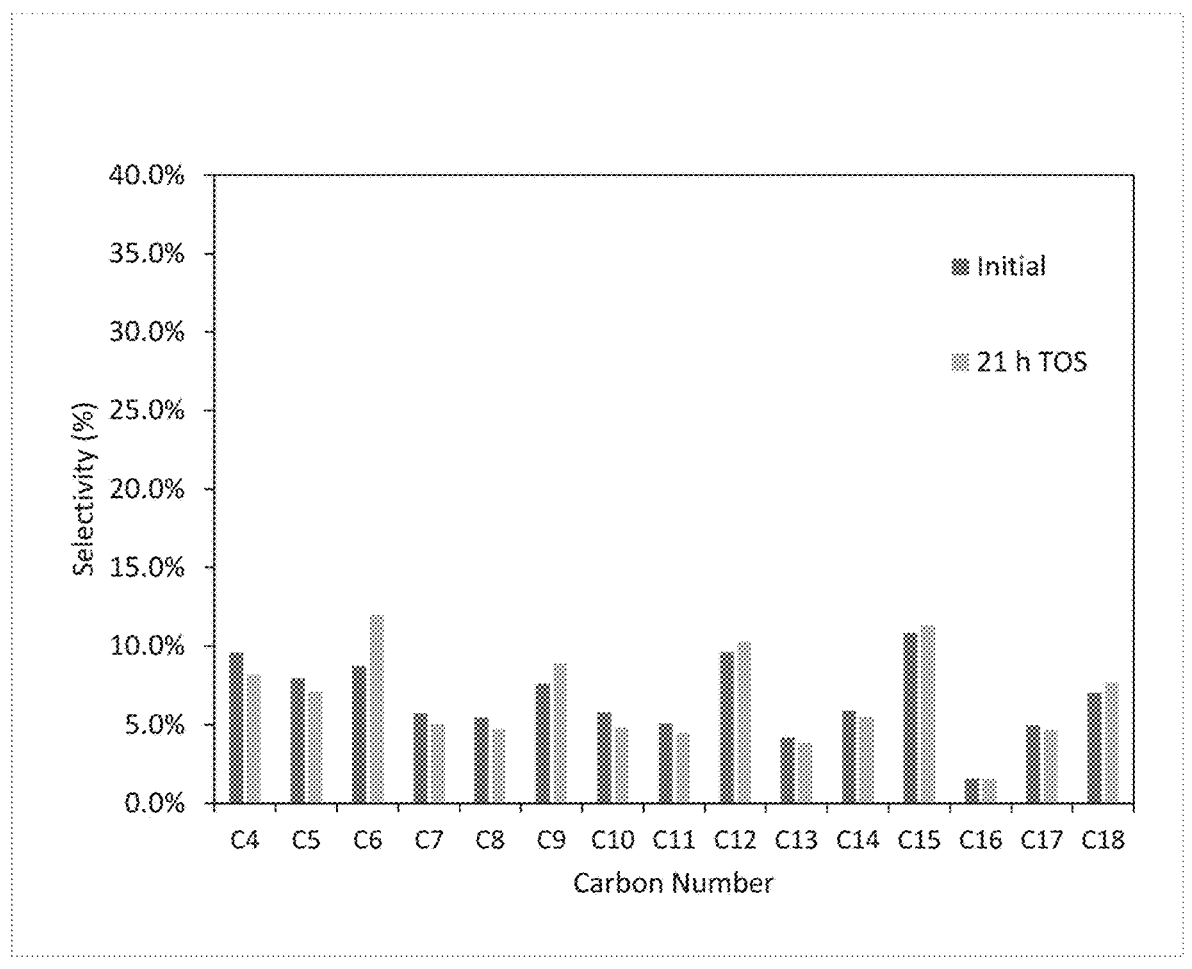

FIG. 7 depicts product distributions at initial time-on-stream (1 h) and 21 h time-on-stream of MFI CATALYST 2/SL1-070 (reaction condition: 260° C., propene partial pressure 165 kPa, space velocity 0.4 (mol $C_3H_6$) (mol $H^+$)$^{-1}$ s$^{-1}$).

Figure 8:
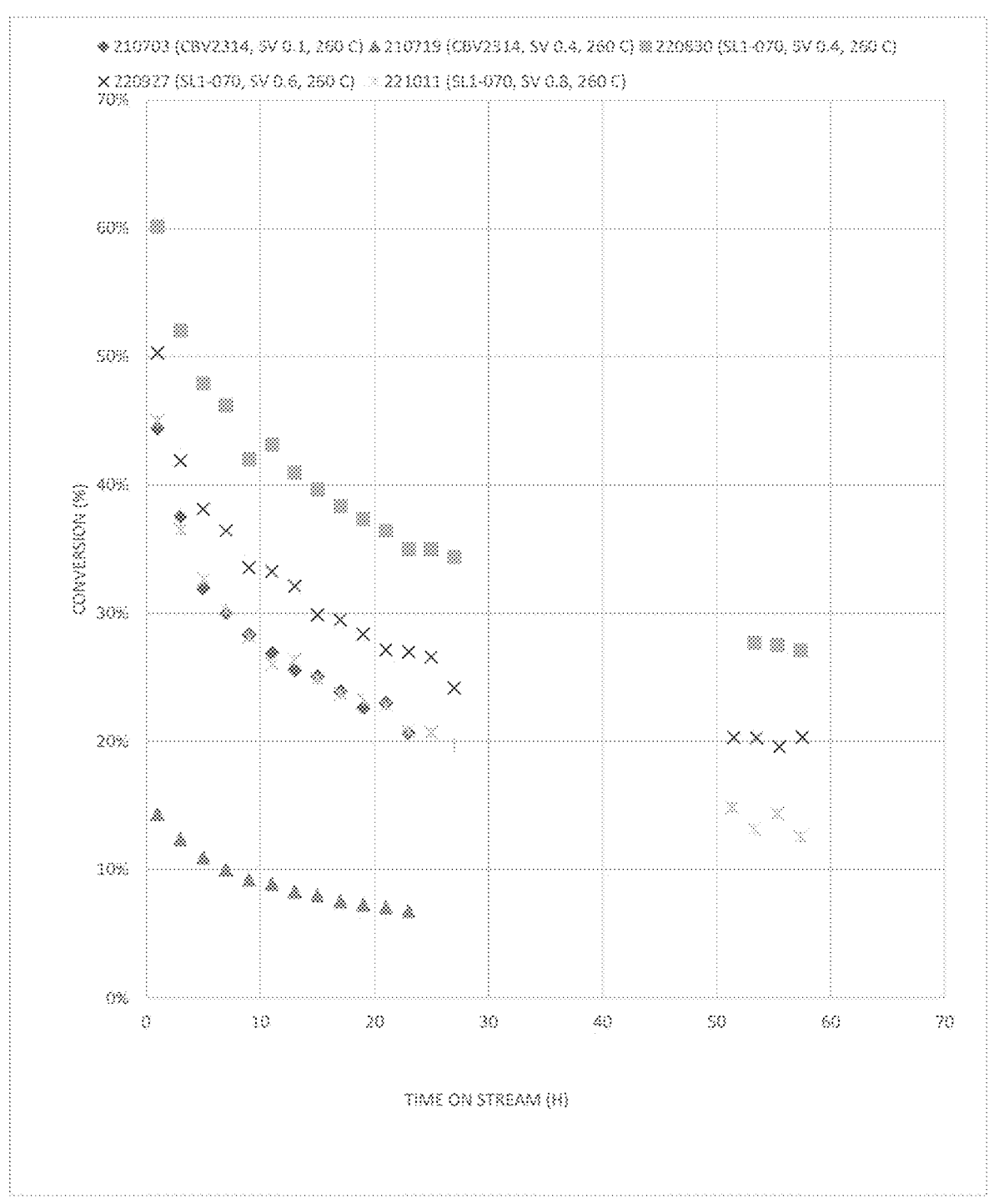

FIG. 8 depicts time-on-stream conversion of propene oligomerization on CBV2314 and MFI CATALYST 2/SL1-070 (reaction condition: 260° C., propene partial pressure 165 kPa, space velocities of 0.1-0.8 (mol $C_3H_6$) (mol $H^+$)$^{-1}$ s$^{-1}$).

Figure 9A:
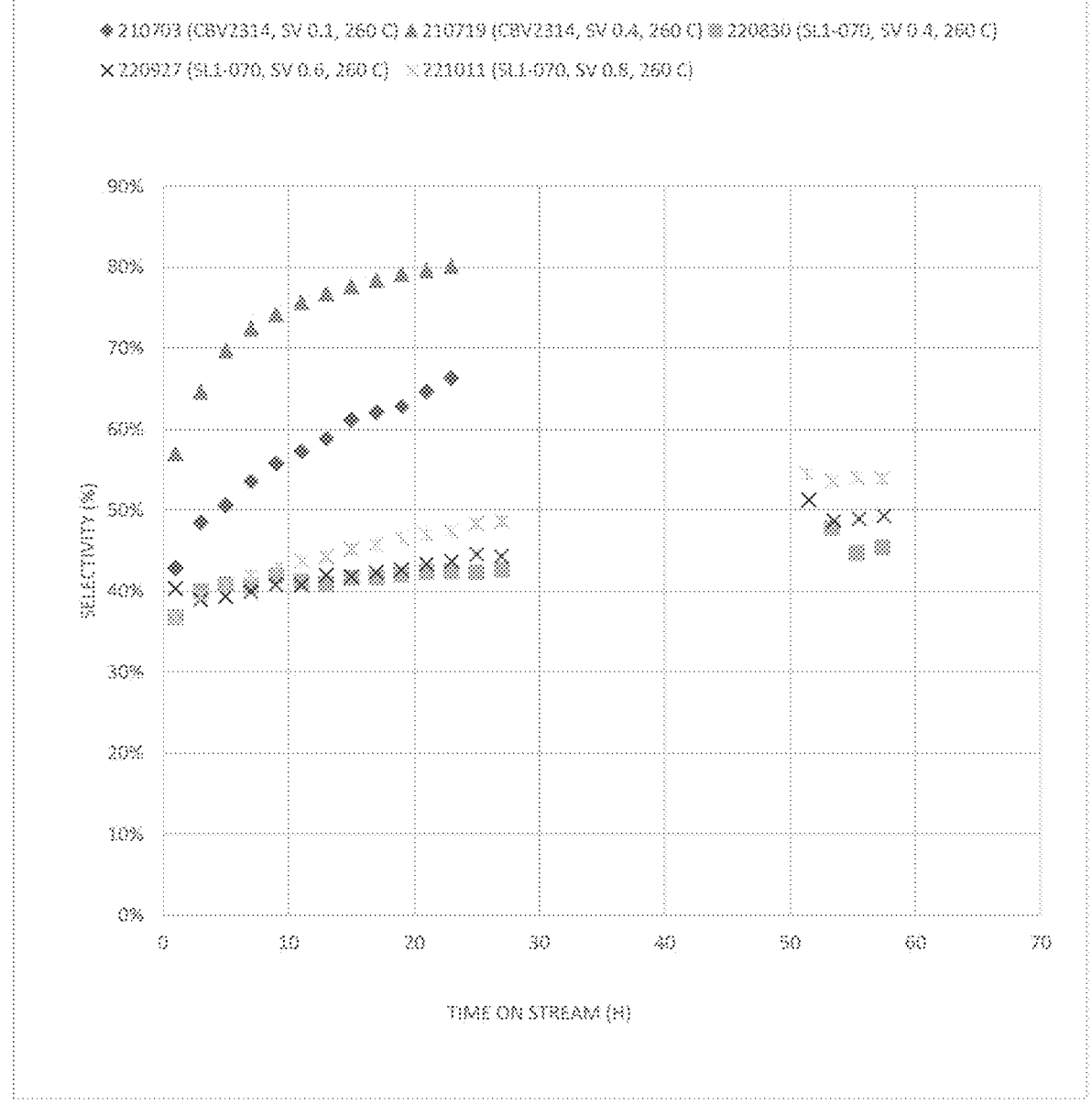
Figure 9B:
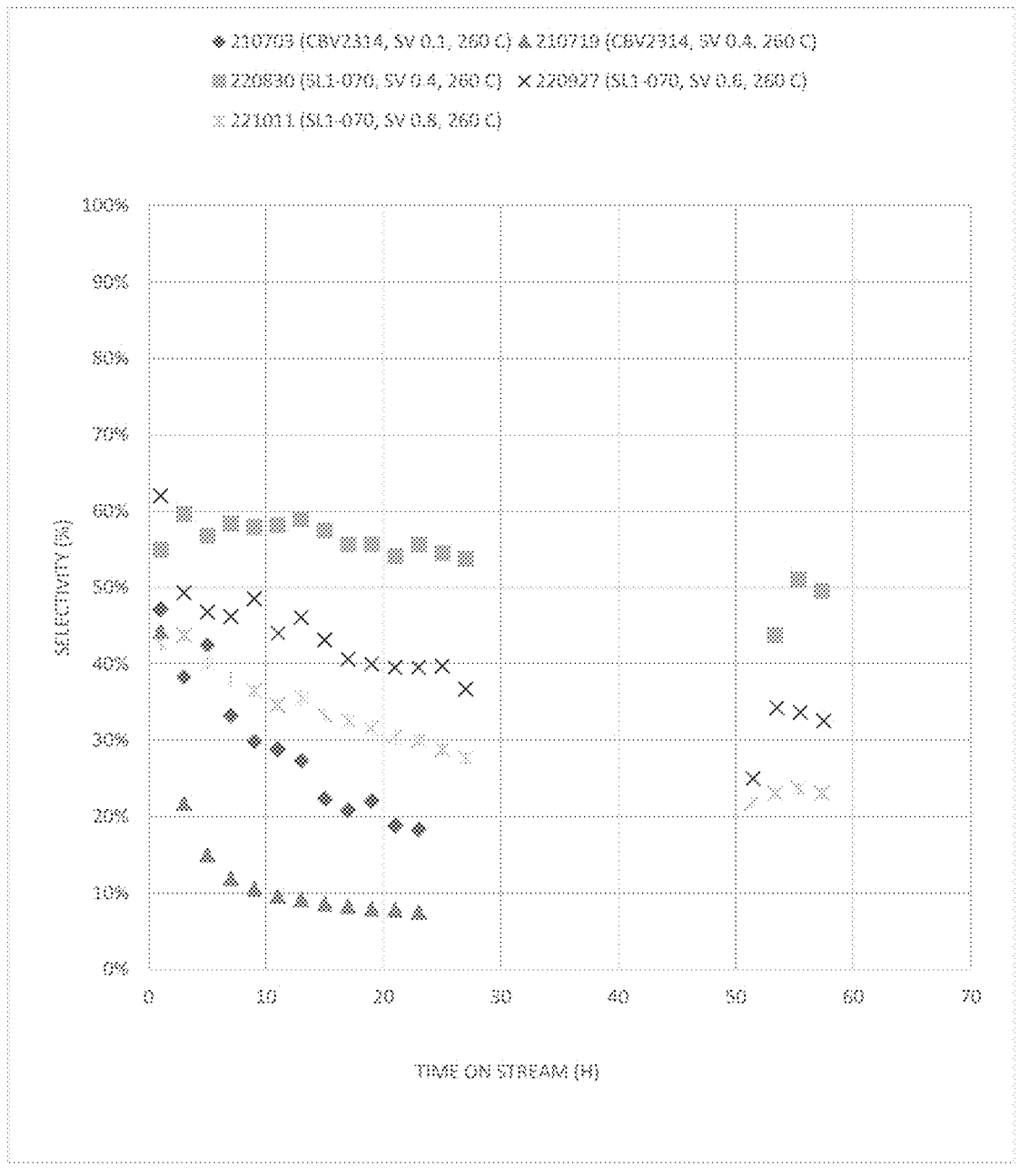

FIG. 9A and FIG. 9B depict time-on-stream selectivity to (FIG. 9A) primary oligomerization products ($C_6$, $C_9$, $C_{12}$, $C_{15}$) and (FIG. 9B) oligomers with carbon number >10 ($C_{10+}$) for CBV2314 and MFI CATALYST 2/SL1-070 measured at different space velocities.

Figure 10A:
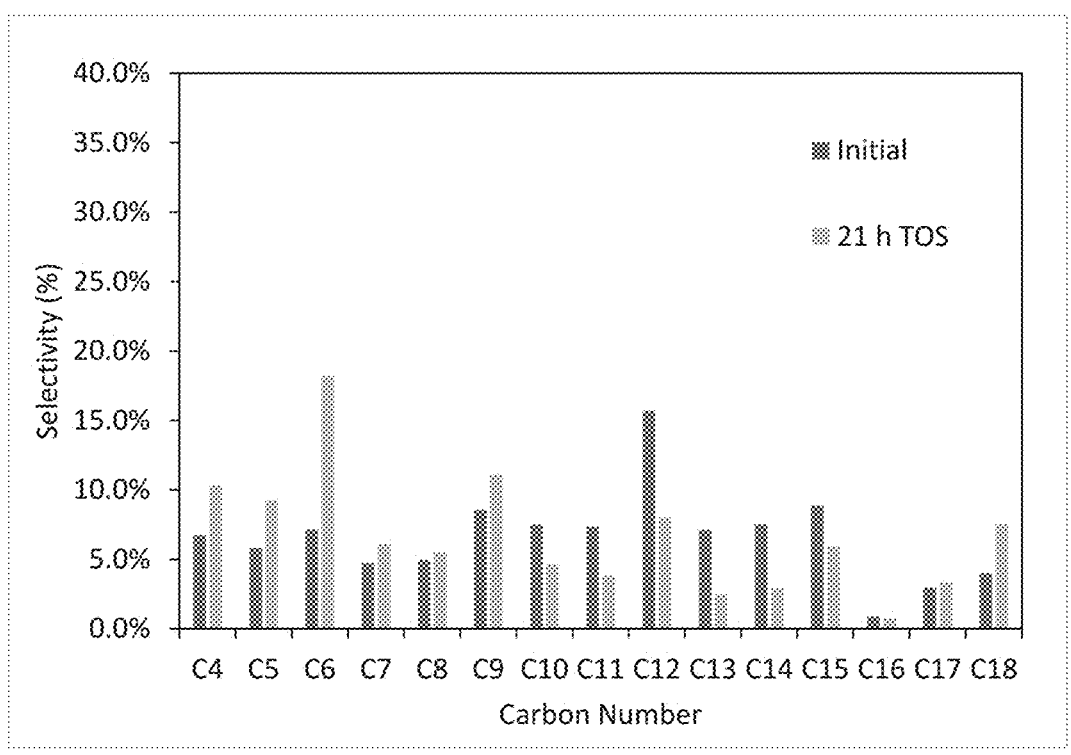
Figure 10B:
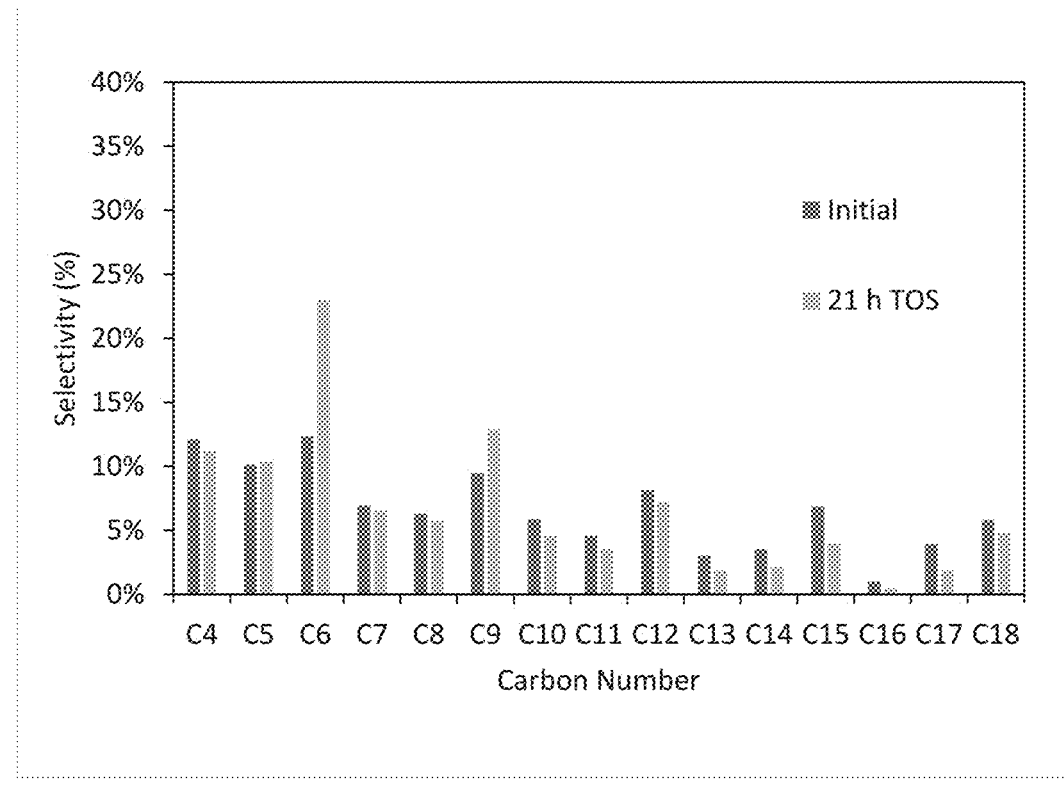

FIG. 10A and FIG. 10B depict product distributions at initial time-on-stream (1 h) and 21 h time-on-stream of MFI CATALYST 2/SL1-070 at different space velocity of (FIG. 10A) 0.6 (mol $C_3H_6$) (mol $H^+$)$^{-1}$ s$^{-1}$ and (FIG. 10B) 0.8 (mol $C_3H_6$) (mol $H^+$)$^{-1}$ s$^{-1}$ (reaction condition: 260° C., propene partial pressure 165 kPa).

Figure 11A:
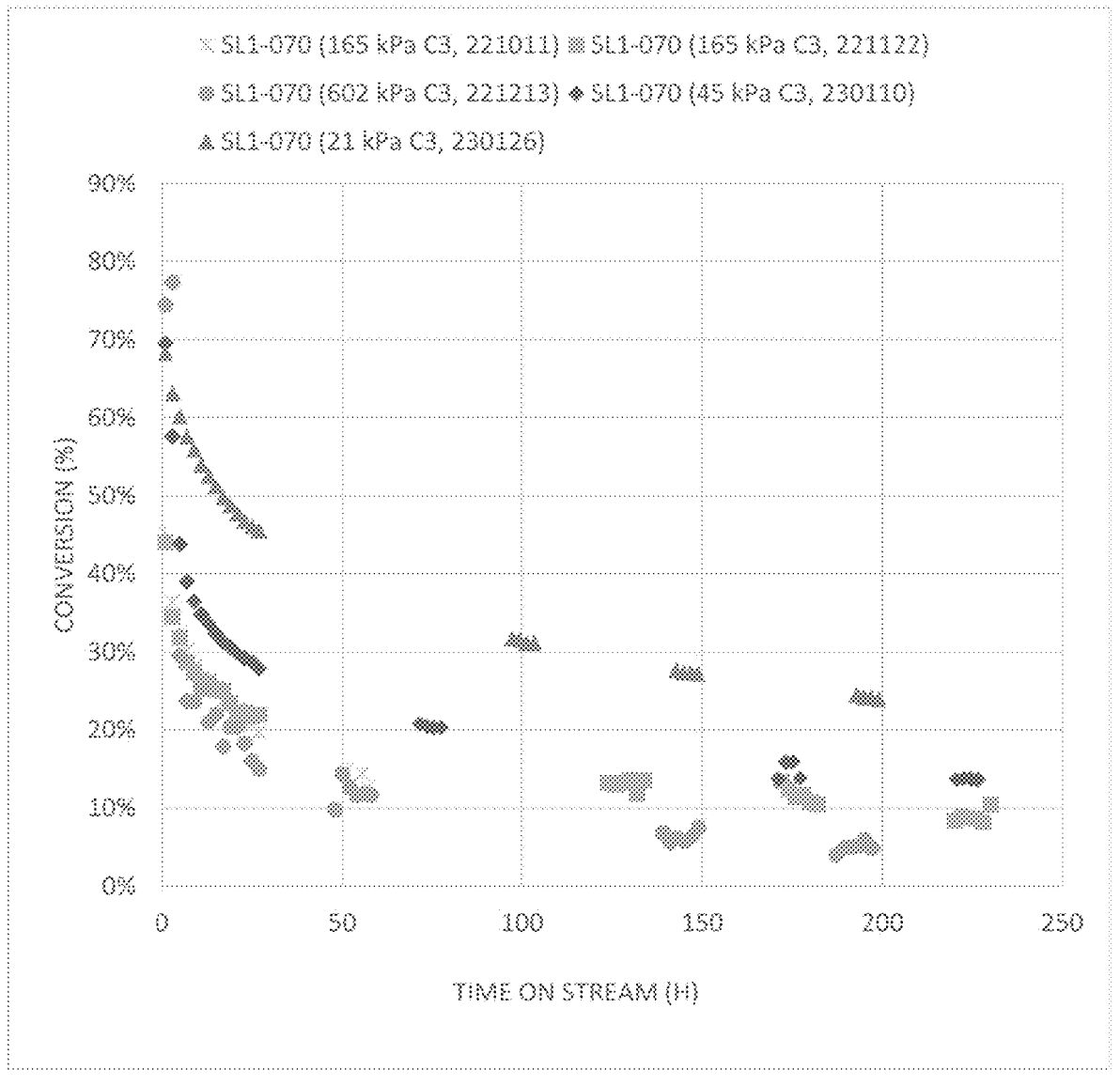
Figure 11B:
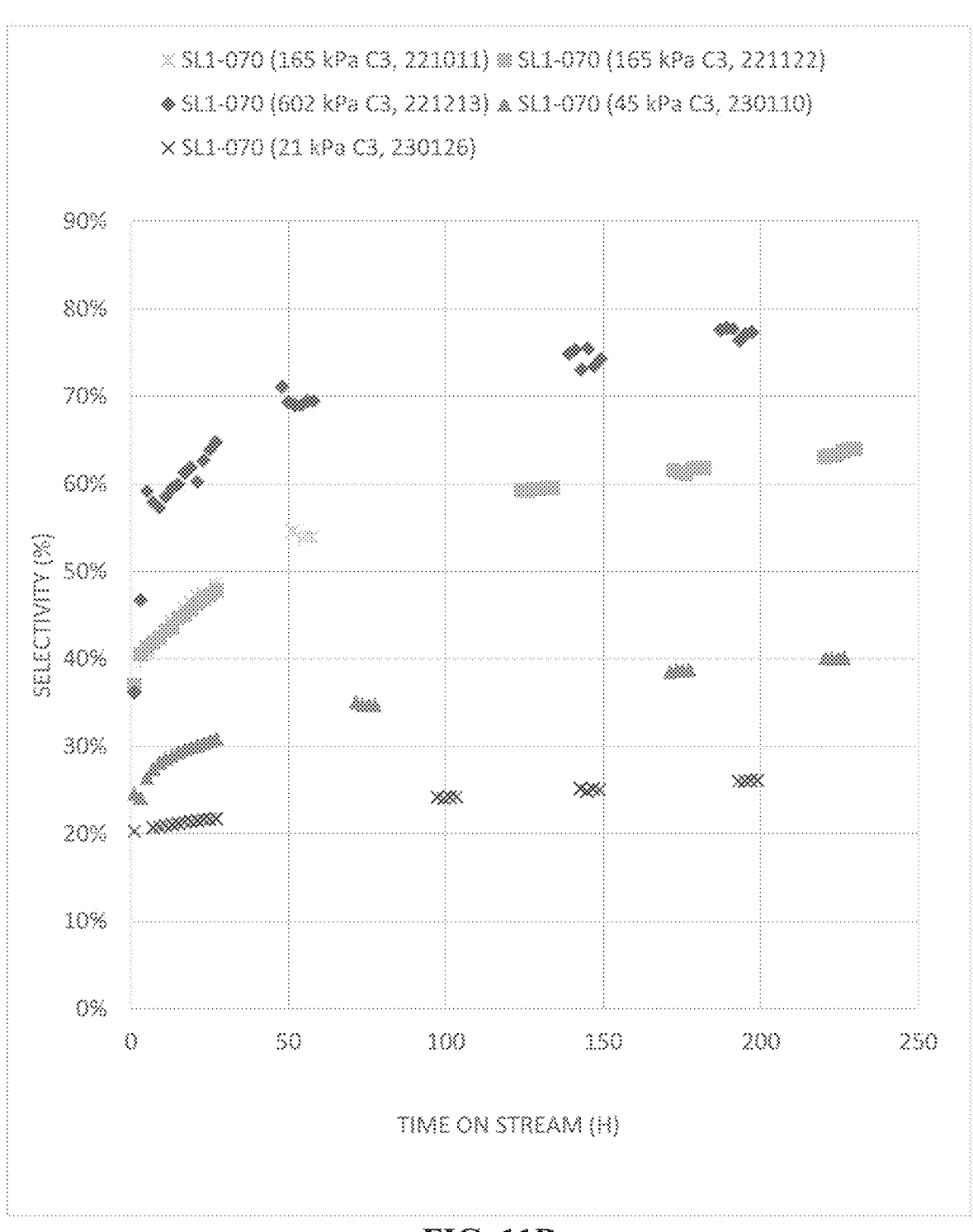
Figure 11C:
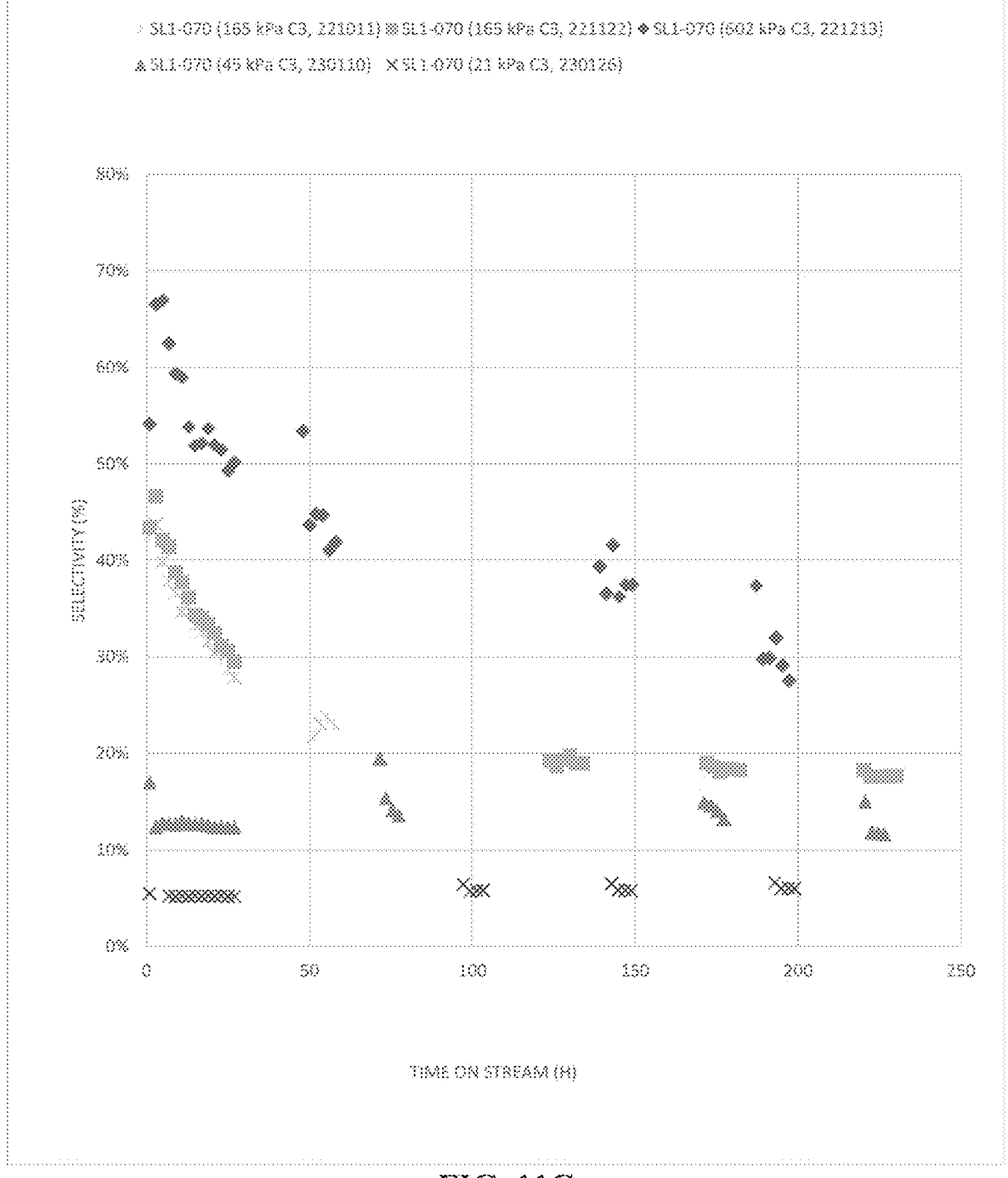

FIG. 11A, FIG. 11B, and FIG. 11C depict propene oligomerization reaction data measured on MFI CATALYST 2/SL1-070 (reaction condition: 260° C., propene partial pressures of 165 kPa, 602 kPa, 45 kPa, 21 kPa, space velocity of 0.8 (mol $C_3H_6$) (mol $H^+$)$^{-1}$ s$^{-1}$) for the (FIG. 11A) time-on-stream conversion, (FIG. 11B) time-on-stream selectivity to primary oligomerization products ($C_6$, $C_9$, $C_{12}$, $C_{15}$) and (FIG. 11C) time-on-stream selectivity to oligomers with carbon number >10 ($C_{10+}$).

Figure 12A:
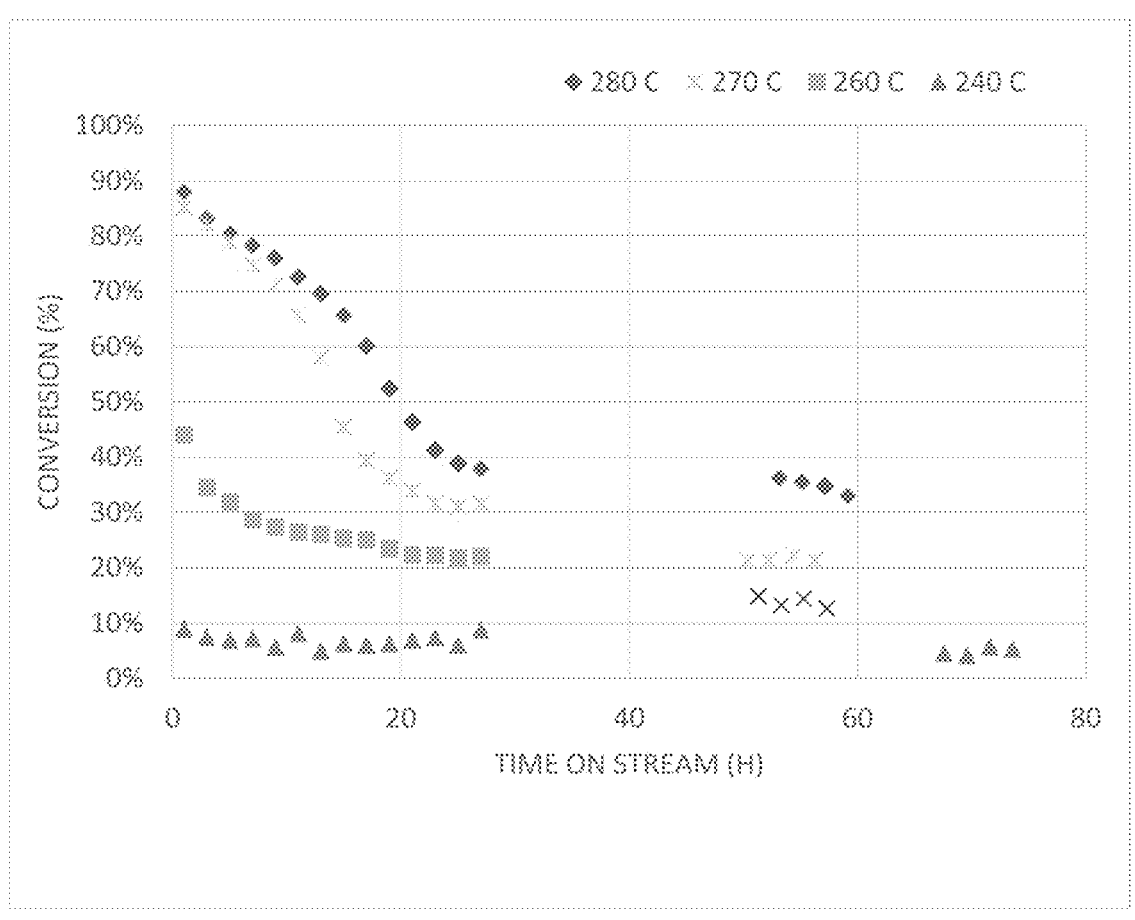
Figure 12B:
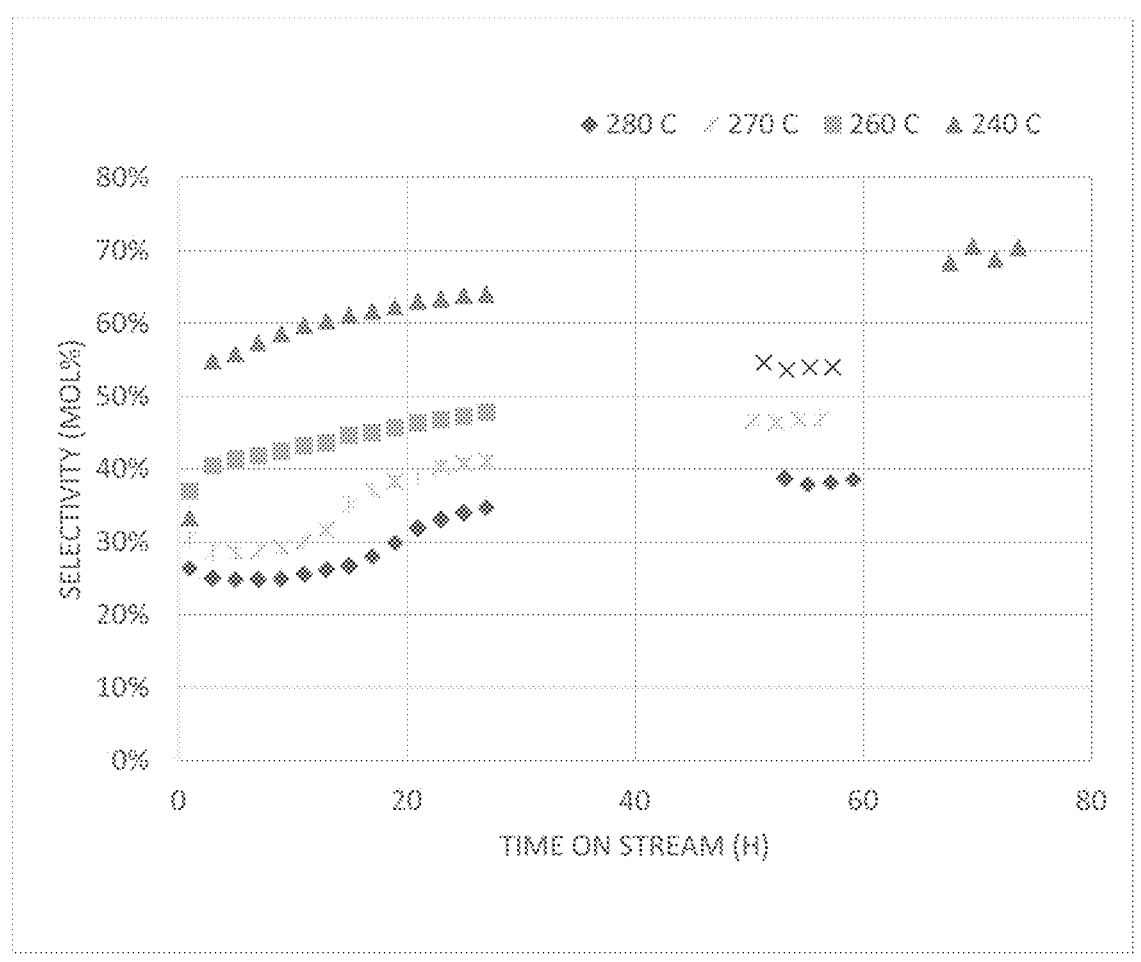
Figure 12C:
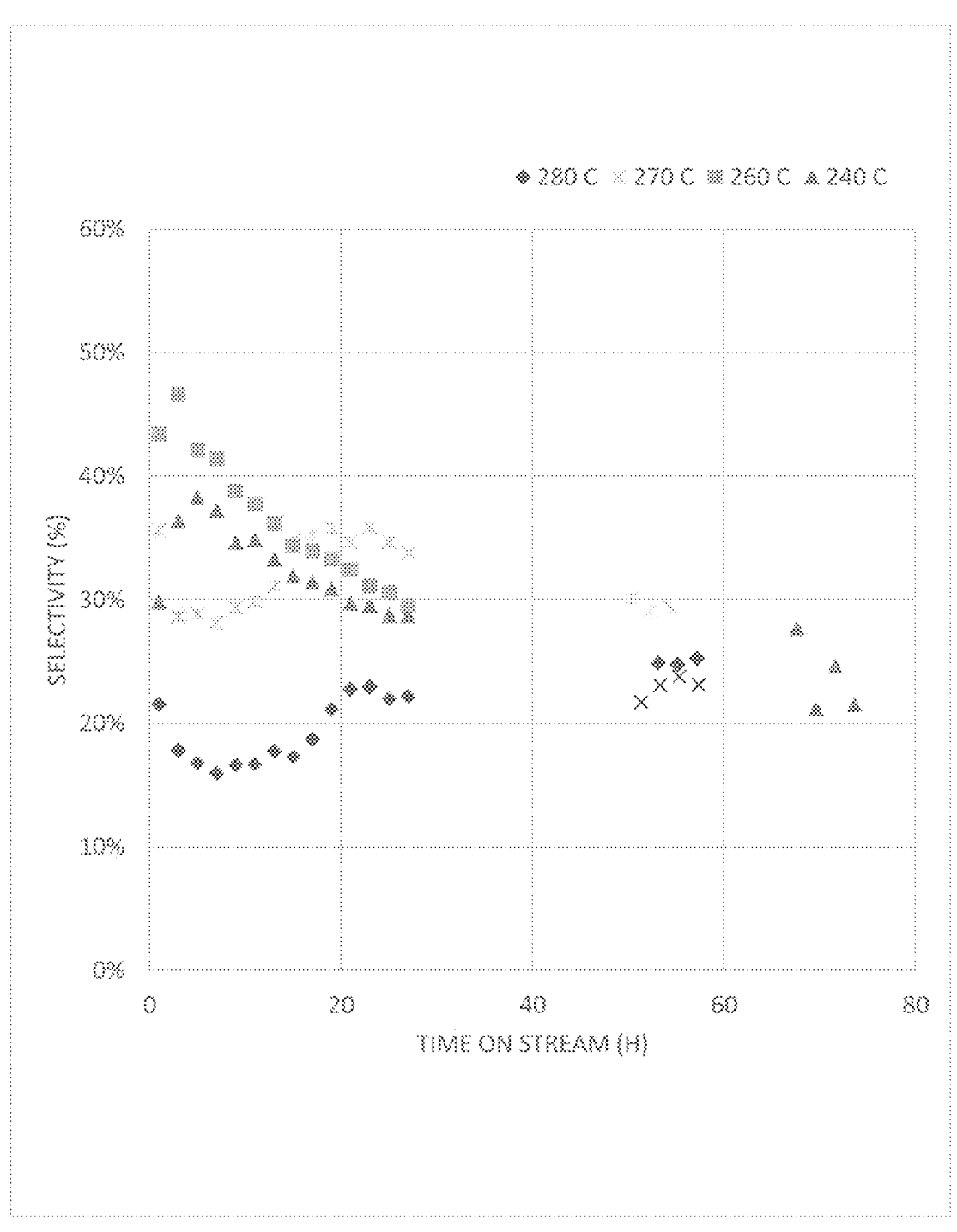

FIG. 12A, FIG. 12B, and FIG. 12C depict propene oligomerization reaction data measured on MFI CATALYST 2/SL1-070 (reaction condition: 240° C., 260° C., 270° C., and 280° C., propene partial pressure 165 kPa, space velocity of 0.8 (mol $C_3H_6$) (mol $H^+$)$^{-1}$ s$^{-1}$) for the (FIG. 12A) time-on-stream conversion, (FIG. 12B) time-on-stream selectivity to primary oligomerization products ($C_6$, $C_9$, $C_{12}$, $C_{15}$) and (FIG. 12C) time-on-stream selectivity to oligomers with carbon number >10 ($C_{10+}$).

Figure 13:
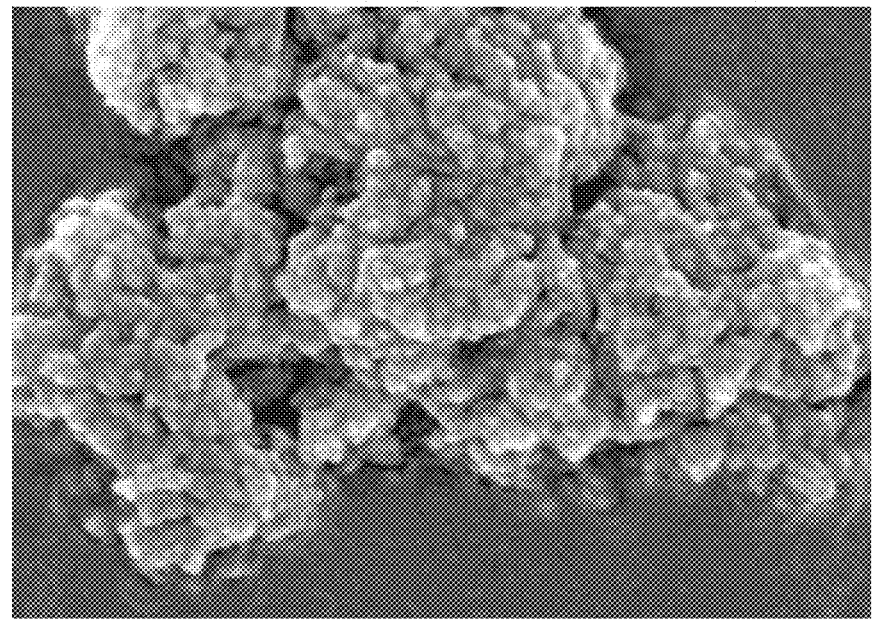

FIG. 13 depicts an SEM image of a third MFI sample synthesized at Purdue University (MFI CATALYST 3/SL2-078).

Figure 14A:
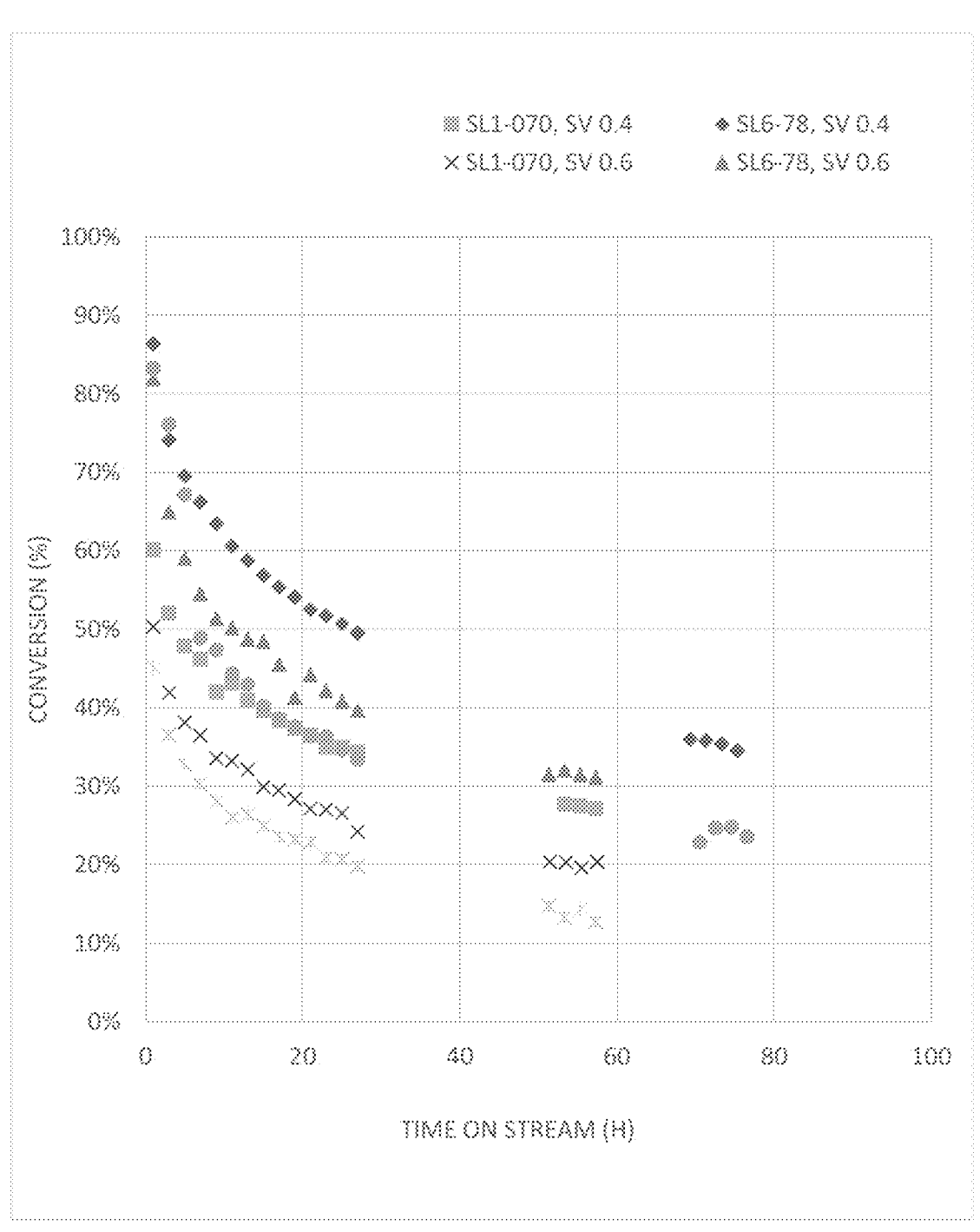
Figure 14B:
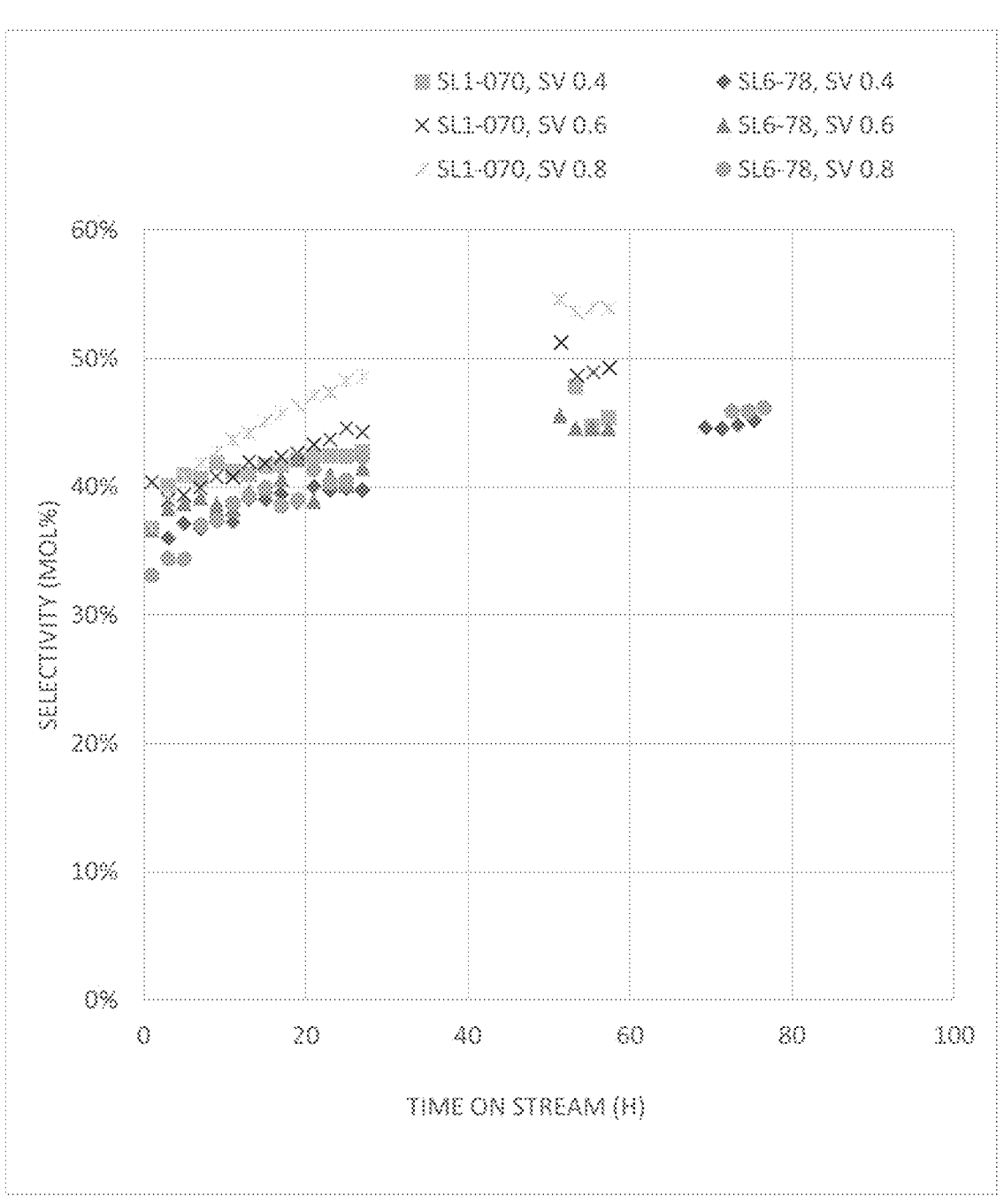
Figure 14C:
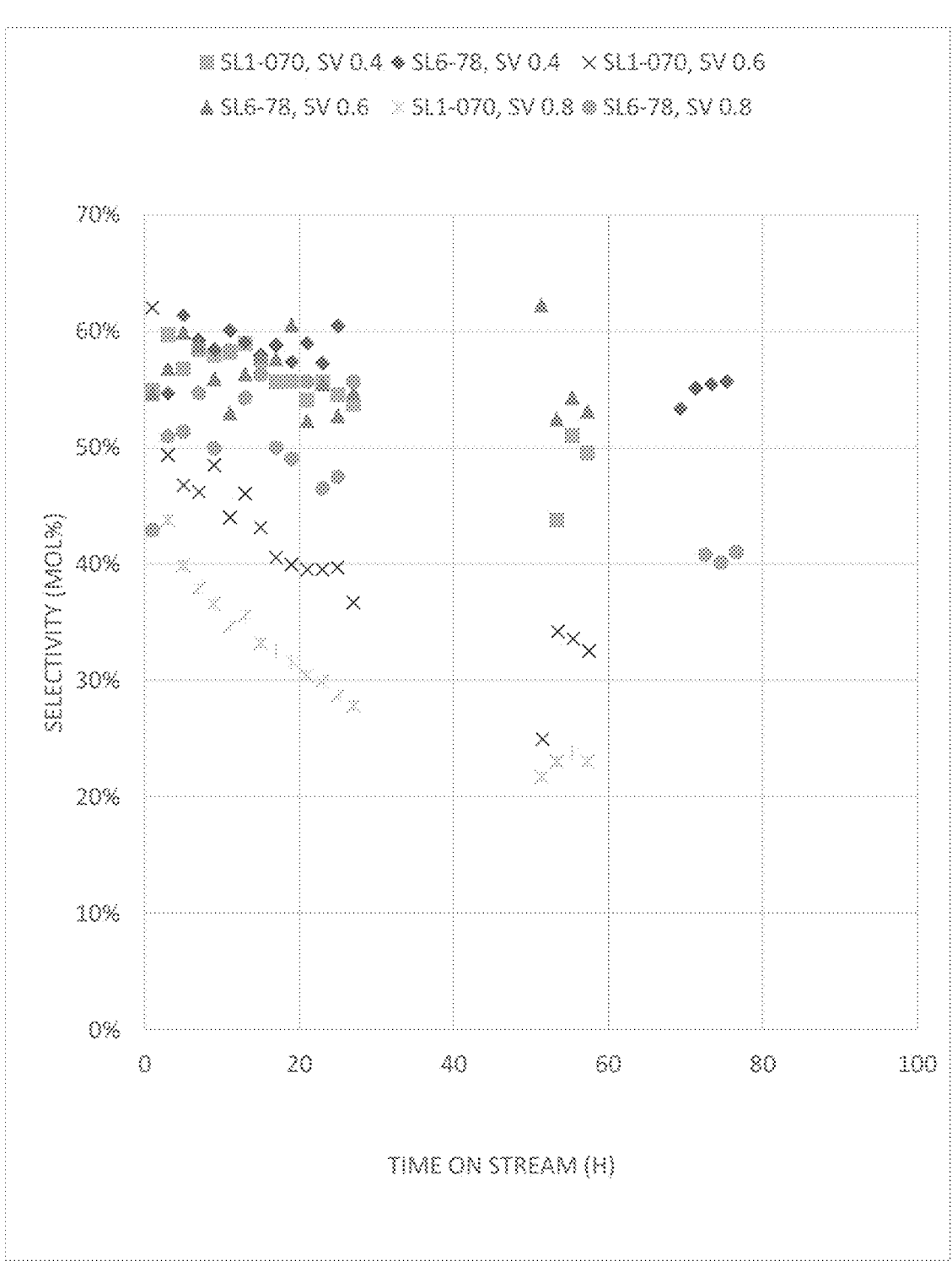

FIG. 14A, FIG. 14B, and FIG. 14C depict propene oligomerization reaction data measured on MFI CATALYST 2/SL1-070 and MFI CATALYST 3/SL2-078 (reaction condition: 260° C., propene partial pressure of 165 kPa, and space velocities of 0.4-0.8 (mol $C_3H_6$) (mol $H^+$)$^{-1}$ s$^{-1}$) for the (FIG. 14A) time-on-stream conversion, (FIG. 14B) time-on-stream selectivity to primary oligomerization products ($C_6$, $C_9$, $C_{12}$, $C_{15}$) and (FIG. 14C) time-on-stream selectivity to oligomers with carbon number >10 ($C_{10+}$).

Figure 15A:
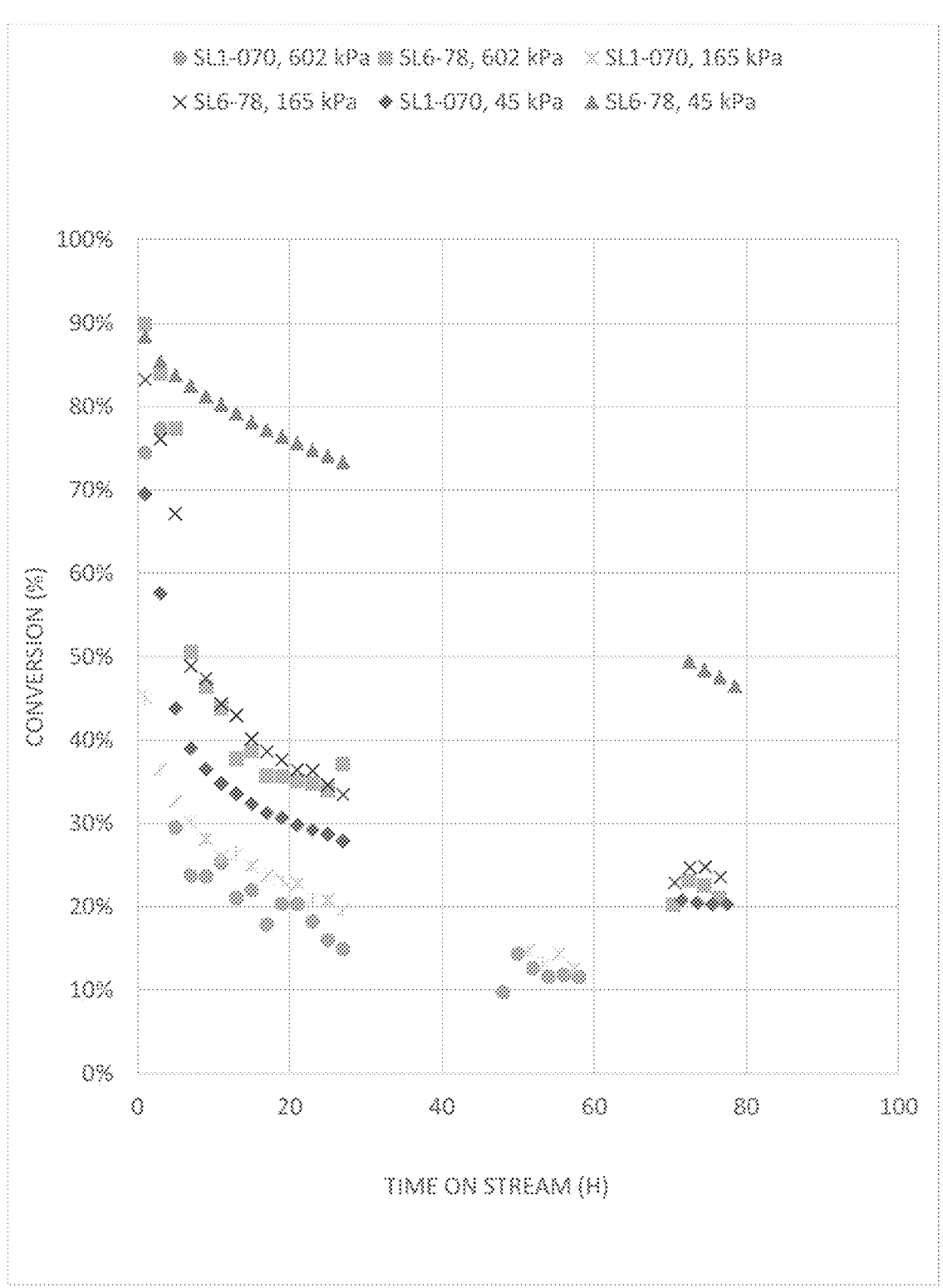
Figure 15B:
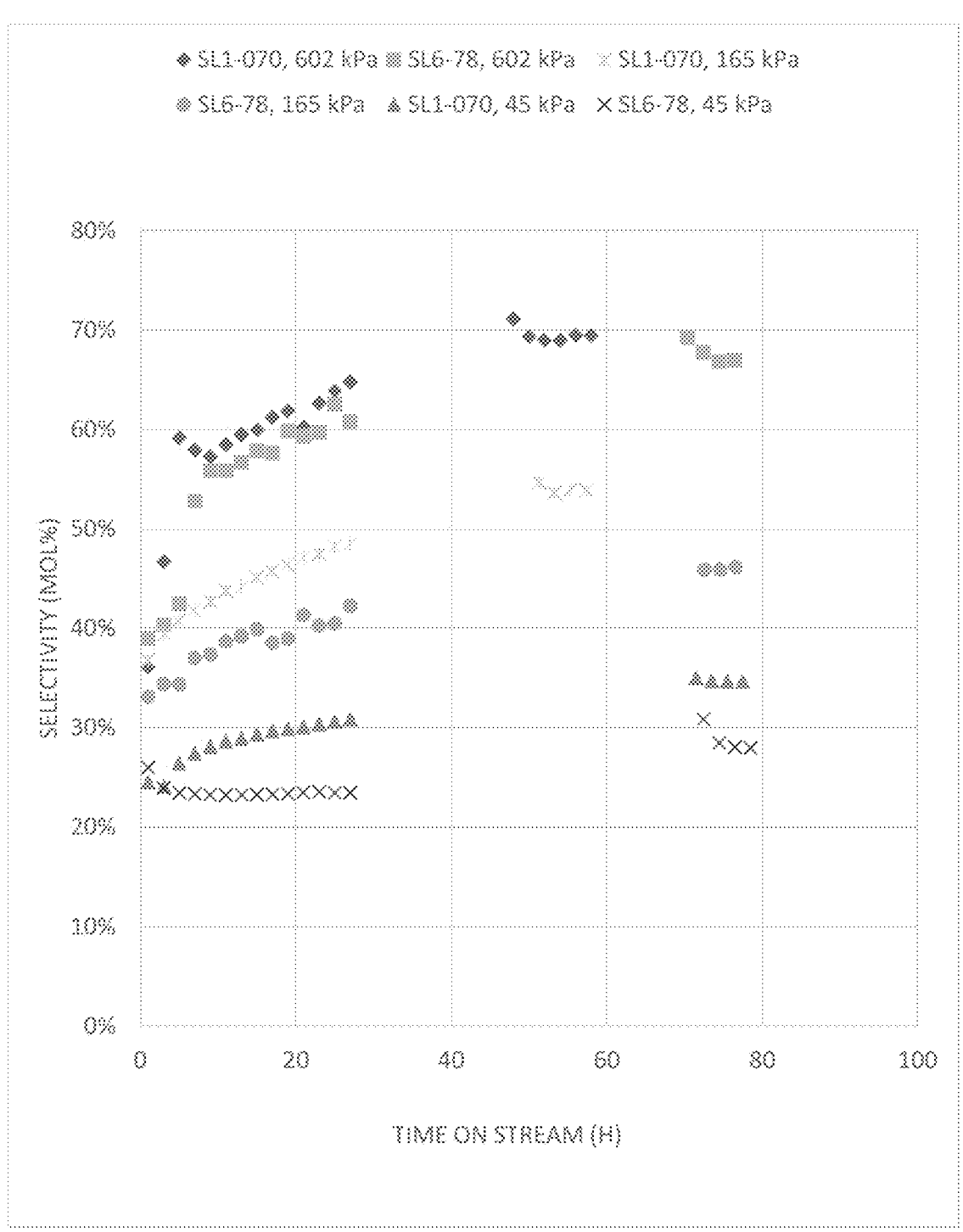
Figure 15C:
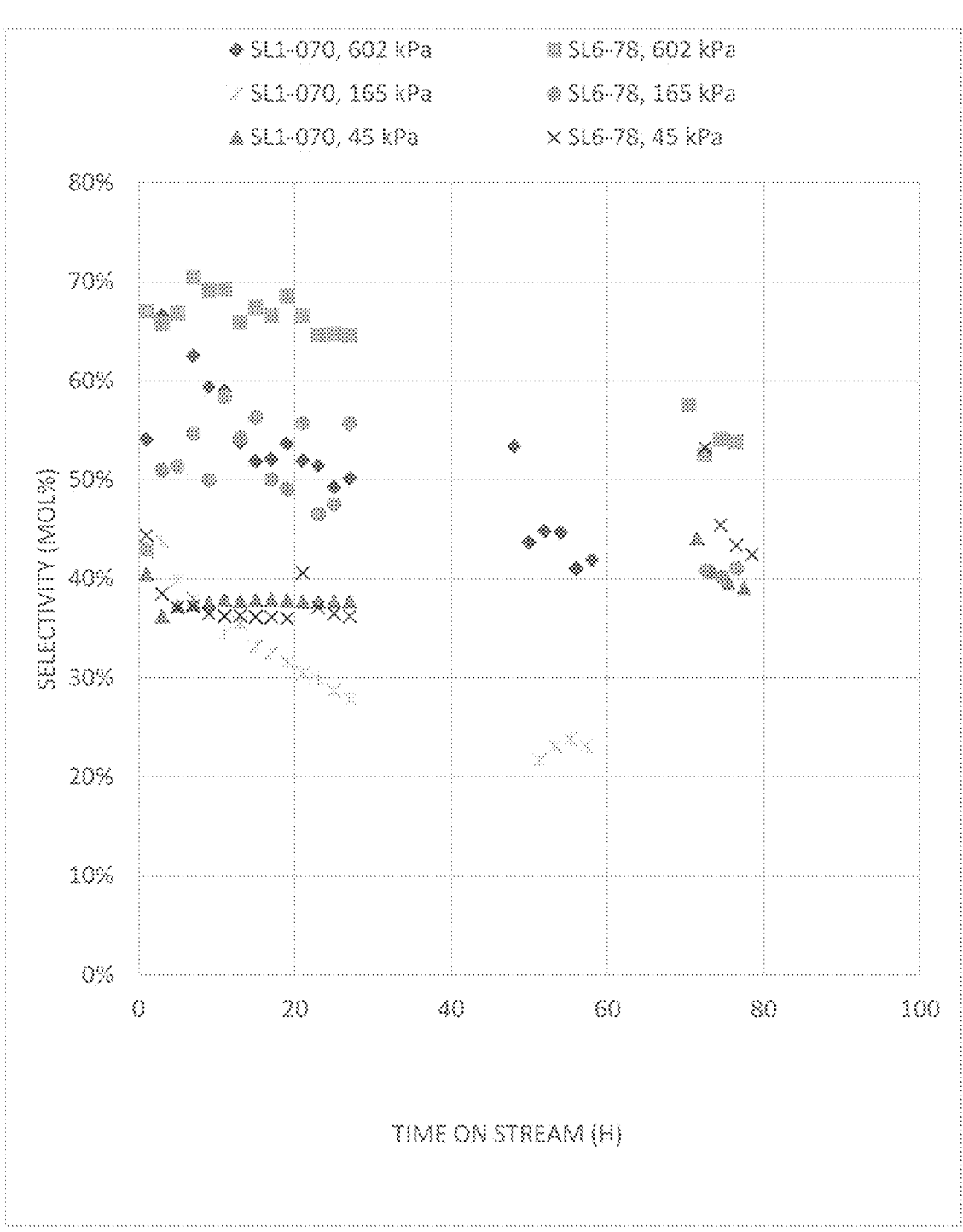

FIG. 15A, FIG. 15B, and FIG. 15C depict propene oligomerization reaction data measured on MFI CATALYST 2/SL1-070 and MFI CATALYST 3/SL2-078 (reaction condition: 260° C., propene partial pressures of 165 kPa, 602 kPa, 45 kPa, and space velocity of 0.8 (mol $C_3H_6$) (mol $H^+$)$^{-1}$ s$^{-1}$) for the (FIG. 15A) time-on-stream conversion, (FIG. 15B) time-on-stream selectivity to primary oligomerization products ($C_6$, $C_9$, $C_{12}$, $C_{15}$) and (FIG. 15C) time-on-stream selectivity to oligomers with carbon number >10 ($C_{10+}$).

Figure 16A:
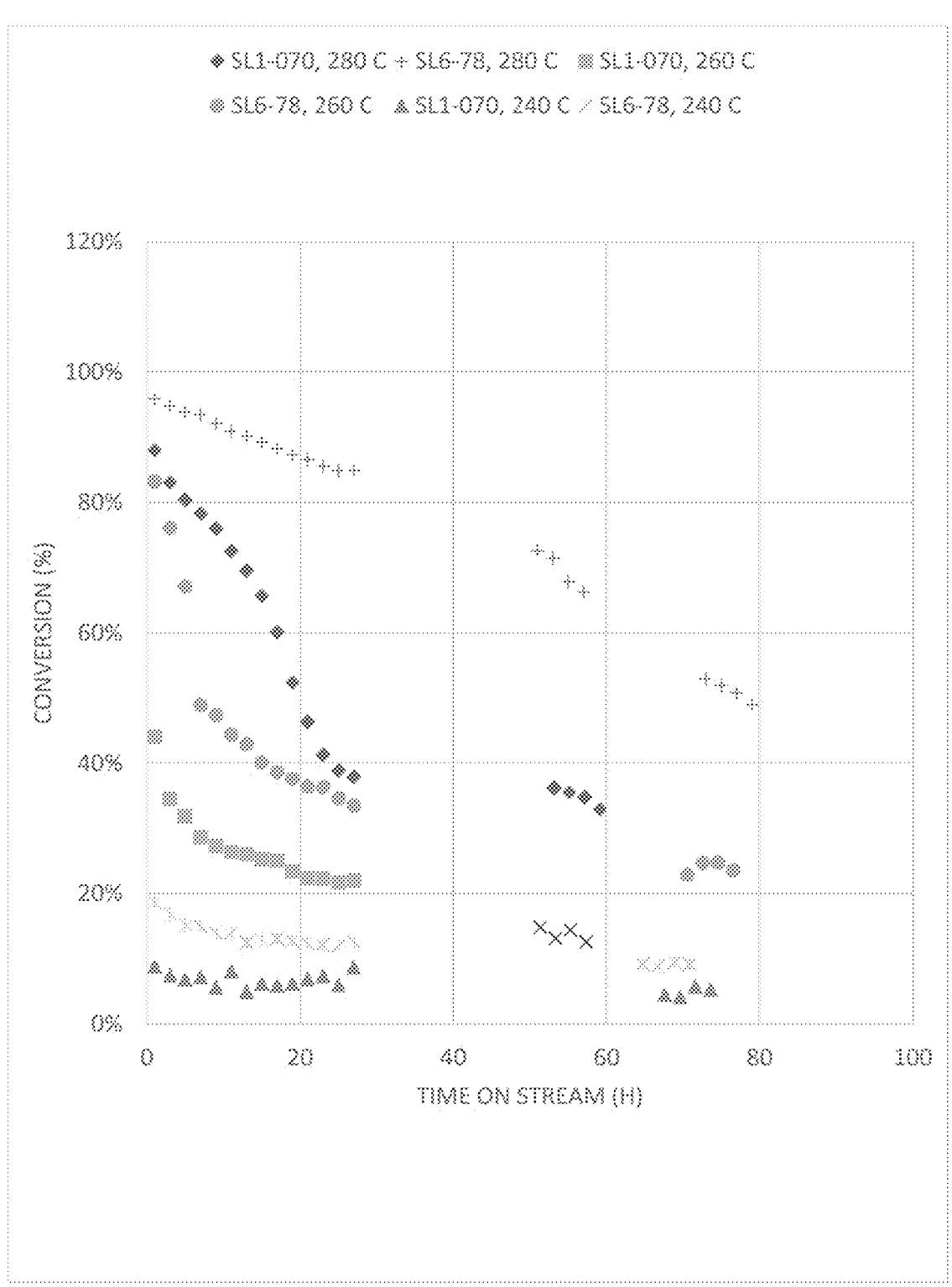
Figure 16B:
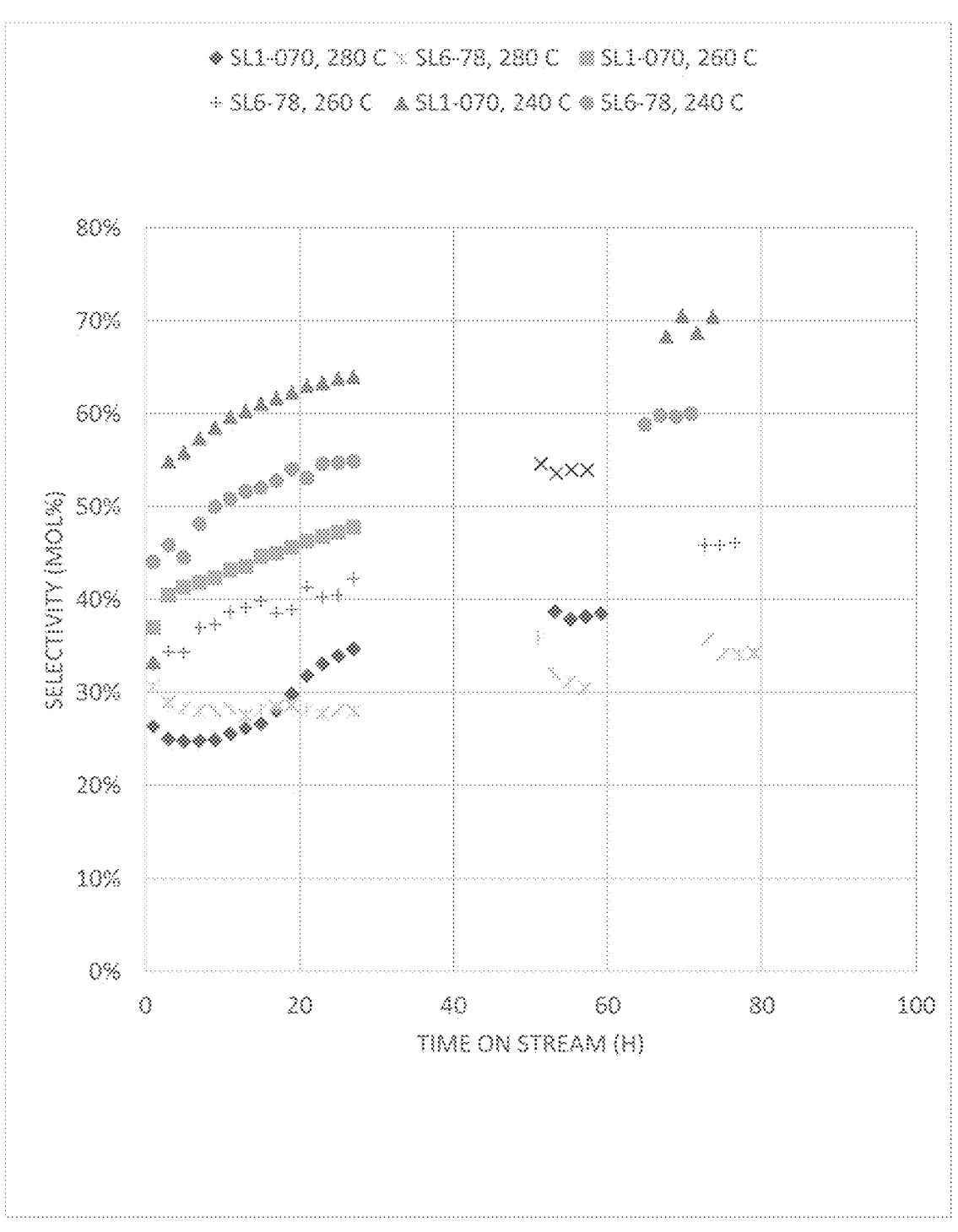
Figure 16C:
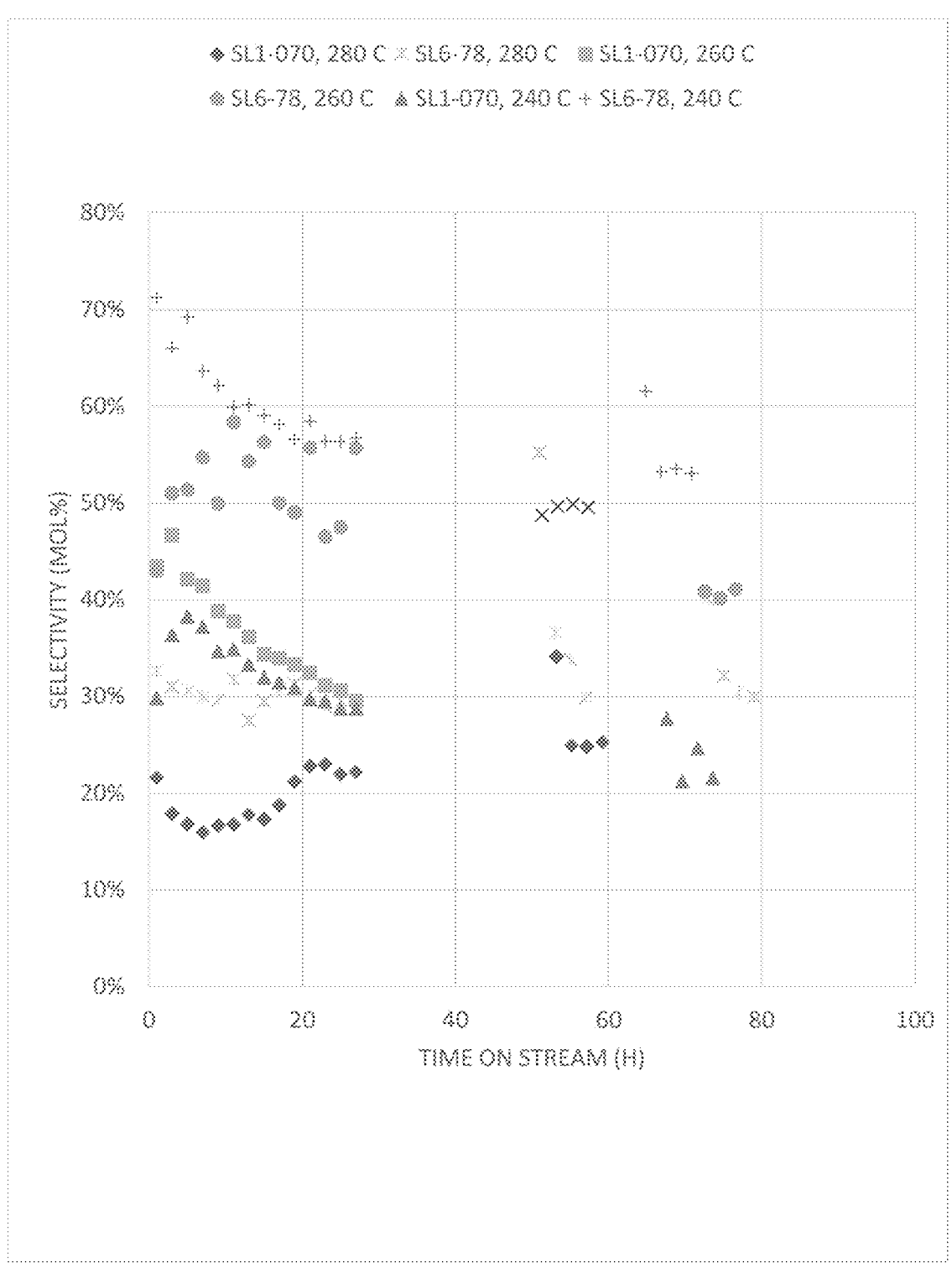

FIG. 16A, FIG. 16B, and FIG. 16C depict propene oligomerization reaction data measured on MFI CATALYST 2/SL1-070 and MFI CATALYST 3/SL2-078 (reaction condition: temperatures of 240° C., 260° C., 280° C., propene partial pressure of 165 kPa, and space velocity of 0.8 (mol $C_3H_6$) (mol $H^+$)$^{-1}$ s$^{-1}$) for the (FIG. 16A) time-on-stream conversion, (FIG. 16B) time-on-stream selectivity to primary oligomerization products ($C_6$, $C_9$, $C_{12}$, $C_{15}$) and (FIG. 16C) time-on-stream selectivity to oligomers with carbon number >10 ($C_{10+}$).

DETAILED DESCRIPTION

It is to be understood that the following disclosure describes several exemplary embodiments for implementing different features, structures, or functions of the invention. Exemplary embodiments of components, arrangements, and configurations are described below to simplify the present disclosure; however, these exemplary embodiments are provided merely as examples and are not intended to limit the scope of the invention. Additionally, the present disclosure can repeat reference numerals and/or letters in the various embodiments and across the figures provided herein. This repetition is for the purpose of simplicity and clarity and does not in itself dictate a relationship between the various embodiments and/or configurations. Moreover, the exemplary embodiments presented below can be combined in any combination of ways, i.e., any element from one exemplary embodiment can be used in any other exemplary embodiment, without departing from the scope of the disclosure.

Additionally, certain terms are used throughout the following description and claims to refer to particular components. As one skilled in the art will appreciate, various entities can refer to the same component by different names, and as such, the naming convention for the elements described herein is not intended to limit the scope of the invention, unless otherwise specifically defined herein. Further, the naming convention used herein is not intended to distinguish between components that differ in name but not function.

Furthermore, in the following discussion and in the claims, the terms "including" and "comprising" are used in an open-ended fashion, and thus should be interpreted to mean "including, but not limited to." The phrase "consisting essentially of" means that the described/claimed composition does not include any other components that will materially alter its properties by any more than 5% of that property, and in any case does not include any other component to a level greater than 3 mass %.

Unless otherwise indicated, all numerical values are "about" or "approximately" the indicated value, meaning the values take into account experimental error, machine tolerances and other variations that would be expected by a person having ordinary skill in the art. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for making the measurement.

The term "or" is intended to encompass both exclusive and inclusive cases, i.e., "A or B" is intended to be synonymous with "at least one of A and B," unless otherwise expressly specified herein.

The indefinite articles "a" and "an" refer to both singular forms (i.e., "one") and plural referents (i.e., one or more) unless the context clearly dictates otherwise. For example, embodiments using "an olefin" include embodiments where one, two, or more olefins are used, unless specified to the contrary or the context clearly indicates that only one olefin is used.

The term "oligomerization" refers to the formation of an oligomer from molecules of lower relative molecular mass. The term "oligomer" refers to dimers, trimers, tetramers, and other molecular complexes having less than 26 repeating units. Oligomers provided herein are typically gases or liquids at ambient temperature, and can include low melting solids, including waxes, at ambient temperature. In some embodiments, the oligomers provided herein can have an atomic weight or molecular weight of less than 10,000 AMU (Da), such as about 5,000 or less, 1,000 or less, 500 or less, 400 or less, 300 or less, or 200 or less. The molecular weight of the oligomer, for example, can range from a low of about 50, 250 or 350 to a high of about 500, 3,000, 7,000, or 9,000 AMU (Da).

The terms "alkane" and "paraffin" are used interchangeably and both refer to any saturated molecule containing hydrogen and carbon atoms only, in which all the carbon-carbon bonds are single bonds and are saturated with hydrogen. Such saturated molecules can be linear, branched, and/or cyclic.

The terms "alkene" and "olefin" are used interchangeably and both refer to any unsaturated molecule containing hydrogen and carbon atoms only, in which one or more pairs of carbon atoms are linked by a double bond. Such unsaturated molecules can be linear, branched, or cyclic, and can include one, two, three or more pairs of carbon atoms linked by double bounds (i.e. mono-olefins, di-olefins, tri-olefins, etc).

The term "wt %" means percentage by weight, "vol %" means percentage by volume, "mol %" means percentage by mole, "ppm" means parts per million, and "ppm wt" and "ppmw" are used interchangeably and mean parts per million on a weight basis. All concentrations herein, unless otherwise stated, are expressed on the basis of the total amount of the composition in question.

Each of the appended claims defines a separate invention, which for infringement purposes is recognized as including equivalents to the various elements or limitations specified in the claims. Depending on the context, all references to the "invention" may in some cases refer to certain specific embodiments only. In other cases, it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this disclosure is combined with publicly available information and technology.

A detailed description of the MFI zeolites and methods for making and using the same will now be provided. ZSM-5 zeolites with low aluminum contents (i.e., high Si/Al ratios)

and small crystallite sizes are provided herein. It has been surprisingly and unexpectedly discovered that time-on-stream product selectivity during propene oligomerization was found to be significantly more stable, as the crystallite size of MFI zeolites decreased. It has also been surprisingly and unexpectedly discovered that as MFI zeolite catalysts deactivate with time-on-stream, there is a shift in product selectivity toward primary oligomerization products (e.g., dimer and trimer products), and this becomes more pronounced as the crystallite size of MFI zeolites increase.

The synthesized MFI zeolite (ZSM-5) can be obtained with smaller crystallite sizes by adapting conventional crystallization techniques and using quaternary ammonium surfactants with hydrocarbon chains ($C_nH_{2n+1}$—$N^+(CH_3)_2$—$C_6H_{12}$—$N^+(CH_3)_2$—$C_nH_{2n+1}$, n=4-8) as the structure directing agent (SDA), such as reported in an earlier publication by Kim et al. *J. Catal.* 288 (2012) 115-123. The preparation method involves adding a source of quaternary ammonium surfactant with hydrocarbon chains and a source of Na to water to form an aqueous solution; homogenizing the aqueous solution for a first time period; adding a source of aluminum to the homogenized aqueous solution to form an intermediate agent and homogenizing the intermediate agent for a second time period to form an aluminum-containing intermediate agent; adding a source of silicon to the aluminum-containing intermediate agent to form an aluminosilicate-containing intermediate agent and homogenizing the aluminosilicate-containing intermediate agent for a third time period to form a synthesis gel; subjecting the synthesis gel to a crystallization process to crystallize a MFI zeolite; and then recovering the solids (e.g., by centrifugation) followed by washing, drying and a high temperature air treatment and subsequent ion-exchange treatments to remove any unreacted reagents or SDA compounds, thereby recovering the acid-form zeolite.

A preferred crystallite size is about 0.001 µm to about 0.1 µm, more preferably about 0.01 µm to about 0.05 µm. Other crystallite sizes (in microns) can range from a low of about 0.001, about 0.005, or about 0.01 to a high of about 0.05, about 0.075, or about 0.1.

The ratio of (quaternary ammonium surfactant with hydrocarbon chains):Si can range from a low value of about 0.05, 0.06, or 0.07 to a high value of about 0.10, 0.15 or 0.20.

The Na:Al ratio can range from a low value of about 0.1 to a high value of 0.3.

The Si:Al ratio can range from a low value of about 20, 30, or 40 to a high value of about 50, 80, or 100.

The source of aluminum can be aluminum hydroxide, aluminum sulfate, aluminum nitrate, aluminosilicate, and any combinations or derivatives thereof.

The source of silicon can be colloidal silica, a silicon alkoxide compound, fumed silica, amorphous silica, aluminosilicate, and any combinations or derivatives thereof.

Each of first, second and third time periods can be the same or different, and each can range from about 1 second to about 48 hours; or about 1 to about 20 hrs; or about 2 to about 10 hrs; or about 3 to about 8 hrs; or about 3 to about 5 hrs; or about 3 to about 4 hrs.

The crystallization process preferably occurs at about 130° C. to about 150° C., but can range from a low of about 60° C., 70° C., 80° C. or 90° C. to a high of about 150° C., 180° C., 200° C. or 240° C. The crystallization process can also take place at about 100° C., 130° C., 140° C., 150° C., 160° C., 170° C., or 180° C.

The high temperature air treatment can occur at about 450° C. to about 550° C. The air treatment but can also range from a low of about 400° C., 410° C., or 420° C. to a high of about 500° C., 550° C. or 600° C.

The support material can have a surface area in the range of from about 10 m²/g to about 700 m²/g, a pore volume in the range of from about 0.1 cc/g to about 4.0 cc/g and an average particle size in the range of from about 0.01 µm to about 0.1 µm. More preferably, the support material can have a surface area in the range of from about 50 m²/g to about 500 m²/g, pore volume of from about 0.5 cc/g to about 3.5 cc/g and average particle size of from about 0.02 µm to about 0.05 µm. The surface area can range from a low of about 50 m²/g, 150 m²/g, or 300 m²/g to a high of about 500 m²/g, 700 m²/g, or 900 m²/g. The surface area also can range from a low of about 200 m²/g, 300 m²/g, or 400 m²/g to a high of about 600 m²/g, 800 m²/g, or 1,000 m²/g. The average pore size of the support material can range of from about 10 Å to 1000 Å, about 50 Å to about 500 Å, about 75 Å to about 350 Å, about 50 Å to about 300 Å, or about 75 Å to about 120 Å.

MFI (ZSM-5) zeolites with low aluminum contents can be synthesized using conventional techniques using tetrapropylammonium hydroxide (TPAOH) as the SDA. These MFI zeolites can be prepared by adding a tetrapropylammonium hydroxide to water to form an aqueous solution; homogenizing the aqueous solution for a first time period; adding a source of aluminum to the homogenized aqueous solution to form an intermediate agent and homogenizing the intermediate agent for a second time period to form an aluminum-containing intermediate agent; adding a source of silicon to the aluminum-containing intermediate agent to form an aluminosilicate-containing intermediate agent and homogenizing the aluminosilicate-containing intermediate agent for a third time period to form a synthesis gel; subjecting the synthesis gel to a crystallization process to crystallize a MFI zeolite; and then recovering the solids (e.g., by centrifugation) followed by washing, drying and a high temperature air treatment and subsequent ion-exchange treatments to remove any unreacted reagents or SDA compounds, thereby recovering the acid-form zeolite.

The amount of TPAOH per gram of silica can range from a low of about 0.5 gr, 0.6 gr, or 0.7 gr to a high of about 1.0 gr, 1.2 gr, or 1.4 gr.

The Si:Al ratio can range from a low of about 80, 100, 120 to high of about 250, 300, 400. The Si:Al ratio can also range from a low of about 85, 125, or 165 to a high of about 275, 350, or 400. The Si:Al ratio can also be 100-400, 15-350, or 200-375.

The source of aluminum can be aluminum hydroxide, aluminum sulfate, aluminum nitrate, aluminosilicate, and any combinations or derivatives thereof.

The source of silicon can be colloidal silica, a silicon alkoxide compound, fumed silica, amorphous silica, aluminosilicate, and any combinations or derivatives thereof.

Each of first, second and third time periods can be the same or different, and each can range from about 1 second to about 48 hours; or about 1 to about 20 hrs; or about 2 to about 10 hrs; or about 3 to about 8 hrs; or about 3 to about 5 hrs; or about 3 to about 4 hrs.

The crystallization process preferably occurs at about 130° C. to about 150° C., but can range from as low of about 60° C., 70° C., 80° C. or 90° C. to a high of about 150° C., 180° C., 200° C. or 240° C. The crystallization process can also take place at about 100° C., 130° C., 140° C., 150° C., 160° C., 170° C., or 180° C.

The high temperature air treatment can occur at about 450 to about 550° C. The air treatment but can also range from as low of about 400° C., 410° C., or 420° C. to a high of about 500° C., 550° C. or 600° C.

The support material can have a surface area in the range of from about 10 m²/g to about 700 m²/g, a pore volume in the range of from about 0.1 cc/g to about 4.0 cc/g and an average particle size in the range of from about 0.05 µm to about 5 µm. More preferably, the support material can have a surface area in the range of from about 50 m²/g to about 500 m²/g, pore volume of from about 0.5 cc/g to about 3.5 cc/g and average particle size of from about 0.1 µm to about 2 µm. The surface area can range from a low of about 50 m²/g, 150 m²/g, or 300 m²/g to a high of about 500 m²/g, 700 m²/g, or 900 m²/g. The surface area also can range from a low of about 200 m²/g, 300 m²/g, or 400 m²/g to a high of about 600 m²/g, 800 m²/g, or 1,000 m²/g. The average pore size of the support material can range of from about 10 Å to 1000 Å, about 50 Å to about 500 Å, about 75 Å to about 350 Å, about 50 Å to about 300 Å, or about 75 Å to about 120 Å.

Oligomerization

The zeolite catalyst, as described herein, can convert one or more light hydrocarbon alkenes to higher molecular weight oligomers. The light hydrocarbons or hydrocarbon feed stream can derive from natural gas, natural gas liquids, or mixtures of both. The hydrocarbon feed stream can be derived directly from shale gas or other formations. The hydrocarbon feed stream can also originate from a refinery, such as from a fluid catalytic cracking (FCC) unit, coker, steam cracker, and pyrolysis gasoline (pygas) as well as alkane dehydrogenation processes, for example, ethane, propane and butane dehydrogenation.

The hydrocarbon feed stream can be or can include one or more olefins having from 2 to 12 carbon atoms. The hydrocarbon feed stream can be or can include one or more linear alpha olefins, such as ethene, propene, butenes, pentenes and/or hexenes. The process is especially applicable to ethene and propene oligomerization for making C4 to about C26 oligomers.

The hydrocarbon feed stream can contain greater than about 65 wt % olefins, such as greater than about 70 wt. % olefins or greater than about 75 wt % olefins. For example, the hydrocarbon feed stream can contain one or more C2 to C12 olefins in amounts ranging from a low of about 50 wt %, 60 wt % or 65 wt % to a high of about 70 wt %, 85 wt % or 100 wt %, based on the total weight of the feed stream. The hydrocarbon feed stream also can include up to 80 mol % alkanes, for example, methane, ethane, propane, butane, and pentane; although the alkane generally comprises less than about 50 mol % of the hydrocarbon feed stream, and preferably less than about 20 mol % of the hydrocarbon stream.

The resulting oligomer(s) can be or can include one or more olefins having from 4 to 26 carbon atoms, such as 12 to 20 carbon atoms, or 16 to 20 carbon atoms. The resulting oligomers, for example, can include butene, hexene, octene, decene, dodecene, tetradecane, hexadecane, octadecene and eicosene and higher olefins, as well as any combinations thereof. The resulting oligomer(s) also can have less than about 5% aromatics and less than about 10 ppm sulfur. The resulting oligomer(s) also can have zero or substantially no aromatics and zero or substantially no sulfur.

The resulting oligomer(s) can be useful as precursors, feedstocks, monomers and/or comonomers for various commercial and industrial uses including polymers, plastics, rubbers, elastomers, as well as chemicals. For example, these resulting oligomer(s) are also useful for making polybutene-1, polyethylene, polypropylene, polyalpha olefins, block copolymers, detergents, alcohols, surfactants, oilfield chemicals, solvents, lubricants, plasticizers, alkyl amines, alkyl succinic anhydrides, waxes, and many other specialty chemicals.

The resulting oligomer(s) can be especially useful for production of diesel and jet fuels, or as a fuel additive. In certain embodiments, the resulting oligomer(s) can have a boiling point in the range of 170° C. to 360° C. and more particularly 200° C. to 300° C. The resulting oligomer(s) also can have a Cetane Index (CI) of 40 to 100 and more particularly 65 to 100. The resulting oligomer(s) also can have a pour point of −50° C. or −40° C.

The oligomerization process can be carried out using any conventional technique. The process can be carried out, for example, in a continuous stirred tank reactor, batch reactor or plug flow reactor. One or more reactors operated in series or parallel can be used. The process can be operated at partial conversion to control the molecular weight of the product and unconverted olefins can be recycled for higher yields.

During oligomerization, the zeolite catalyst can be used alone or can be used with one or more promoters, and/or one or more co-catalysts or activators. The term promoter refers to any metal that can be added to the acid-form zeolite to provide another catalytically active compound, such as nickel. The terms "co-catalyst" and "activator" are used herein interchangeably and refer to any compound, other than the reacting olefin, that can added to the acid-form or metal/acid-form zeolite to further promote the reaction. For example, the following co-catalyst and/or activators can optionally be used: alumoxanes, aluminum alkyls, ionizing activators, which may be neutral or ionic, alumoxane compounds, modified alumoxane compounds, and ionizing anion precursor compounds that abstract one reactive, σ-bound, metal ligand making the metal complex cationic and providing a charge-balancing noncoordinating or weakly coordinating anion. Once the zeolite catalyst is deactivated with high molecular weight carbon, or coke, it can be regenerated using known techniques in the art, including for example, by combustion in air or nitrogen at a temperature of about 400° C. or higher.

EXAMPLES

Embodiments discussed and described herein are further described with the following examples. Although the following examples are directed to specific embodiments, they are not to be viewed as limiting in any specific respect.

In the following examples, three MFI zeolites (MFI CATALYST 1/EB6-053, MFI CATALYST 2/SL1-070, and MFI CATALYST 3/SL2-078) were synthesized with lower aluminum contents (per volume crystallite) and smaller crystallite sizes. These catalysts and a commercially available MFI catalyst were then used to oligomerize propylene. It was surprisingly and expectedly discovered that the product selectivity remained more stable with time-on-stream as the two inventive catalysts deactivated compared to the commercially available MFI zeolite. This is a significant finding that will allow long-term operation of an oligomerization catalyst to produce a product stream of stable composition.

MFI Catalyst (MFI Catalyst 1/EB6-053)

To synthesize the MFI CATALYST 1/EB6-053, water (28 MΩ, 19.57 g) and aluminum nitrate (Al(NO$_3$)$_2$, Aldrich, 98+%, 0.13 g) were combined in a perfluoroalkoxy alkane jar and stirred until homogenized. In a separate jar, tetrapropylammonium hydroxide (TPAOH, Alfa Aesar 40 wt/wt % in H$_2$O, 19.41 g), and tetraethyl orthosilicate (TEOS, Aldrich, 98%, 22.33 g) were combined and stirred until homogenized. These mixtures were combined, stirred at ambient temperature for 22 hours, and then transferred to two 45 mL Teflon-lined stainless-steel autoclaves (Parr Instruments) and placed in a forced convection oven at 423 K for 3 days. After the zeolite crystallization vessel was quenched, all samples were washed 3× with deionized water, 3× with a 50/50 wt % mixture of acetone and water, and 1× with deionized water (~30 cm$^3$ gsample$^{-1}$ per wash) using centrifugation to recover solid material between washes. Washed samples were dried in stagnant air (373 K) and subsequently treated in flowing air at 853 K for 10 h (6.9×10$^{-5}$ mol s$^{-1}$, 0.0167 K s$^{-1}$ UHP, 99.999%, Indiana Oxygen) to remove occluded organic content. 0.5 g of the synthesized zeolite was added to 122 g of 0.8 M ammonium acetate solution and heated while stirring until the solution was heated to 353 K. Then, ammonium fluorosilicate solution (prepared by mixing 0.015 g NH$_4$SiF$_6$ with 5.2 g H$_2$O) was added dropwise into the prepared zeolite solution over the course of 2 h. The mixed solution was stirred at 353 K for 6 h. The ammonium fluorosilicate treated zeolite was then washed with boiling deionized water (ca. 373 K) four times, followed by washing with ambient temperature water one time.

MFI Catalyst (MFI Catalyst 2/SL1-070)

The MFI CATALYST 2/SL1-070 was synthesized using gemini-type quaternary ammonium surfactant which had the chemical formula of (C$_6$H$_{13}$—N$^+$(CH$_3$)$_2$—C$_6$H$_{12}$—N$^+$ (CH$_3$)$_2$—C$_6$H$_{13}$)Br$_2^-$. The synthesis recipe was adapted from the synthesis reported by Kim et al. [J. Catal. 288 (2012) 115-123]. Molar ratio of the synthesis solution was 1 SiO$_2$/0.01 Al$_2$(SO$_4$)$_3$/0.18 Na/0.1 quaternary ammonium surfactant/40 H$_2$O. In a typical synthesis, 0.222 g of aluminum sulfate octadecahydrate (≥97%, Sigma Aldrich) was dissolved in 18.5 g of deionized water (18.2 MΩ cm) in a perfluoroalkoxy alkane (PFA) jar. Next, the dissolved Al$_2$ (SO$_4$)$_3$ solution was added dropwise to 2.40 g of 10 wt % NaOH solution (NaOH, 97 wt %, Sigma-Aldrich, dissolved in deionized water), which was prepared in a separate PFA jar. This mixture was stirred for 5 minutes under ambient conditions. Then, 1.67 g of prepared gemini-type quaternary ammonium surfactant ((C$_6$H$_{13}$—N$^+$(CH$_3$)$_2$—C$_6$H$_{12}$—N$^+$ (CH$_3$)$_2$—C$_6$H$_{13}$)Br$_2$) was added to the mixture and stirred for 5 minutes under ambient conditions. Then, 5.01 g of colloidal silica (Ludox AS40, 40 wt %, Sigma Aldrich) was added to the mixture and stirred for 12 h under ambient conditions. The synthesis solution was then transferred to a 45 ml Teflon-lined stainless steel autoclave (Parr Instruments) and placed in a forced convection oven (Yamato DKN-402C) at 403 K and rotated at 40 rpm for 7 days. The synthesized solids were recovered via centrifugation, washed with deionized water until the pH of the supernatant reached a value below 9. The recovered solids were dried at 373 K for 24 h, and treated in flowing dry air (99.999% UHP, Indiana Oxygen) at 853 K for 10 h (0.0167 K s$^{-1}$).

MFI Catalyst (MFI Catalyst 3/SL2-078)

The MFI CATALYST 3/SL2-078 MFI was synthesized using gemini-type quaternary ammonium surfactant which had the chemical formula of (C$_8$H$_{17}$—N$^+$(CH$_3$)$_2$—C$_6$H$_{12}$— N$^+$(CH$_3$)$_2$—C$_8$H$_{17}$)Br$_2^-$. The synthesis recipe was adapted from the synthesis reported by Kim et al. [J. Catal. 288 (2012) 115-123]. Molar ratio of the synthesis solution was 1 SiO$_2$/0.01 Al$_2$(SO$_4$)$_3$/0.18 Na/0.1 quaternary ammonium surfactant/40 H$_2$O. In a typical synthesis, 0.222 g of aluminum sulfate octadecahydrate (>97%, Sigma Aldrich) was dissolved in 18.5 g of deionized water (18.2 MΩ cm) in a perfluoroalkoxy alkane (PFA) jar. Next, the dissolved $Al_2$ $(SO_4)_3$ solution was added dropwise to 2.40 g of 10 wt % NaOH solution (NaOH, 97 wt %, Sigma-Aldrich, dissolved in deionized water), which was prepared in a separate PFA jar. This mixture was stirred for 5 minutes under ambient conditions. Then, 1.86 g of prepared gemini-type quaternary ammonium surfactant $(C_8H_{17}—N^+(CH_3)_2—C_6H_{12}—N^+$ $(CH_3)_2—C_8H_{17})Br_2^-$ was added to the mixture and stirred for 5 minutes under ambient conditions. Then, 5.01 g of colloidal silica (Ludox AS40, 40 wt %, Sigma Aldrich) was added to the mixture and stirred for 12 h under ambient conditions. The synthesis solution was then transferred to a 45 ml Teflon-lined stainless steel autoclave (Parr Instruments) and placed in a forced convection oven (Yamato DKN-402C) at 403 K and rotated at 40 rpm for 14 days. The synthesized solids were recovered via centrifugation, washed with deionized water until the pH of the supernatant reached a value below 9. The recovered solids were dried at 373 K for 24 h, and treated in flowing dry air (99.999% UHP, Indiana Oxygen) at 853 K for 10 h (0.0167 K s$^{-1}$).

Comparative Catalyst: CBV2314

CBV2314 is a commercially available MFI catalyst that was obtained from Zeolyst International with a nominal Si/Al ratio of 13.

All MFI catalysts were converted into their NH$_4$-form by ion-exchange in aqueous 1M NH$_4$NO$_3$ solution (98%, Sigma Aldrich) for 24 h under ambient conditions, followed by treating the sample in flowing dry air (1.67 cm$^3$ s$^{-1}$ g$_{cat}^{-1}$, 99.999% UHP, Indiana Oxygen) at 773 K (0.0167 K s$^{-1}$) for 4 h to convert to their H-form.

Zeolite Characterization

The crystalline structure of synthesized materials was determined from powder X-ray diffraction (XRD) patterns measured on a Rigaku SmartLab X-ray diffractometer with a Cu Kα source (λ=0.154 nm) operated at 1.76 kW. Diffraction patterns were measured from 4-40° 2θ. All patterns collected were consistent with the MFI topology. Zeolite micropore volumes were calculated from Ar adsorption isotherms collected at 87 K for H-MFI samples in a Micromeritics ASAP 2020 Surface Area and Porosity Analyzer by finding the minimum of the semilogarithmic plot of $\partial(V_{ads})/\partial(\ln(P/P_0))$ versus $\ln(P/P_0)$. All micropore volumes were typical of highly crystalline MFI structure (ca. 0.16 cm$^3$ g$^{-1}$).

Elemental compositions of the samples were analyzed using inductively coupled plasma-optical emission spectroscopy (ICP-OES) with a Thermo Scientific iCAP 7000 Plus Series ICP-OES. Aqueous samples were prepared by dissolving ca. 0.02 g of solid in 2.5 g of hydrofluoric acid (48 wt %, Alfa Aesar). After >24 h, 1 g of HNO$_3$ (70 wt %, Sigma-Aldrich) was added and diluted with 50 g of deionized water.

Crystal sizes of the MFI zeolite samples were estimated with scanning electron microscopy (SEM) on Teneo (FEI) microscope operating at 2 kV. Prior to imaging, samples were coated with platinum to reduce charging of the insulating materials.

Oligomerization of Propylene

Propylene reactions were performed in a stainless-steel reactor (9.5 mm i.d.) equipped with a concentric thermowell (K-type thermocouple) extending through the axial center of the reactor with the tip in the center of the catalyst bed to monitor temperature. In a typical experiment, 0.01-0.15 g of NH$_4$-form zeolite was pelletized and sieved to retain particles of fixed diameter (180-250 μm), and diluted with SiO$_2$ (Sigma-Aldrich, high purity grade 180-250 μm) in zeolite/ SiO$_2$ weight-ratios of 0.03-0.50. This mixture was supported in the reactor by quartz-wool plugs and stainless-steel rods on both sides. The reactor was held within a furnace equipped with a temperature controller. Prior to oligomerization, an oxidative pretreatment (1.7×10$^{-5}$ mol s$^{-1}$ flowing air (air zero, THC <1 ppm) and flowing 5.1×10$^{-5}$ mol s$^{-1}$ He (99.999%, Indiana Oxygen)) was performed by ramping the temperature to 823 K (0.025 K s$^{-1}$) to convert the sample into its H-form before cooling to reaction temperature. Reactant flows were generally composed of 5-95 mol % propene (99.99%, Matheson), 5 mol % methane as an internal standard (99.97%, Matheson), and balance helium (99.999%, Indiana Oxygen). Space velocity was varied by changing the mass of catalyst loaded (0.01-0.15 g) and the flow rate of propene (7×10$^{-6}$-6×10$^{-5}$ mol s$^{-1}$).

Figure 1:
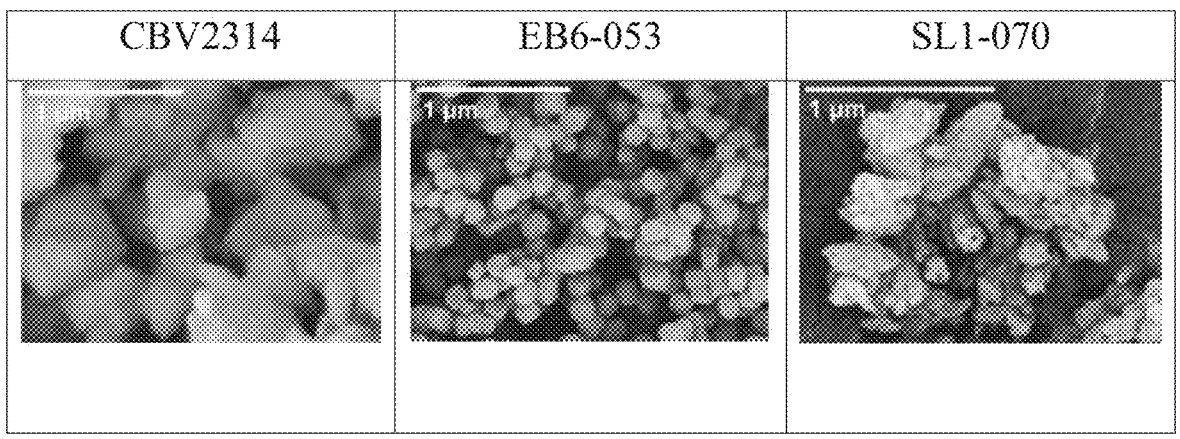
FIG. 1 depicts SEM images of a commercially available MFI sample (CBV2314) and two MFI samples synthesized at Purdue University (MFI CATALYST 1/EB6-053 and MFI CATALYST 2/SL1-070).

Measured Si/Al ratios and crystal sizes for commercially available Al-MFI zeolite and synthesized Al-MFI zeolites are given in Table 1. SEM images of the samples are shown in FIGS. 1 and 13.

TABLE 1

| Catalyst properties of commercial and synthesized MFI | | | |
|---|---|---|---|
| Sample | Si/Al | Active site density, mol H$^+$/g$_{cat}$ | Crystal size, μm |
| CBV2314$^a$ | 13 | 9.94 × 10$^{-4}$ | 0.30 |
| MFI CATALYST 1/EB6-053$^b$ | 300 | 5.53 × 10$^{-5}$ | 0.13 |
| MFI CATALYST 2/SL1-070$^b$ | 47 | 2.66 × 10$^{-4}$ | 0.02 |
| MFI CATALYST 3/SL3-078$^b$ | 47 | 2.58 × 10$^{-4}$ | 0.01 |

$^a$Obtained from Zeolyst International
$^b$Synthesized at Purdue

FIGS. 2-12 and 14-16 show the conversion and selectivities of propene oligomerization using the commercial Al-MFI zeolite and three Al-MFI zeolites synthesized at Purdue. C$_n$ (n=4, 5, . . . , 18) indicates the olefin products containing n carbon atoms.

Figure 2:
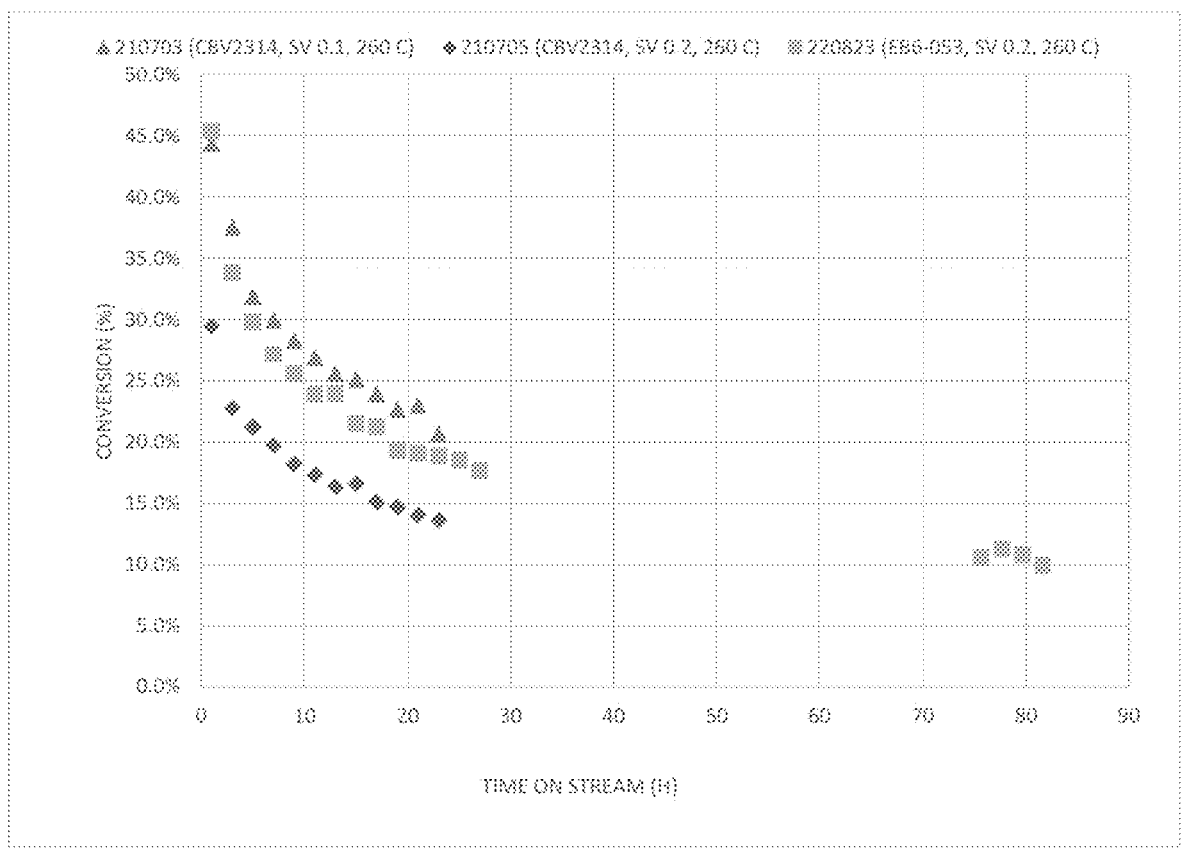
FIG. 2 depicts time-on-stream conversion of propene oligomerization from CBV2314 and MFI CATALYST 1/EB6-053 using reaction conditions: 260° C., propene partial pressure 165 kPa, space velocities of 0.1 and 0.2 (mol $C_3H_6$) (mol $H^+$)$^{-1}$ s$^{-1}$.
Figure 3A:
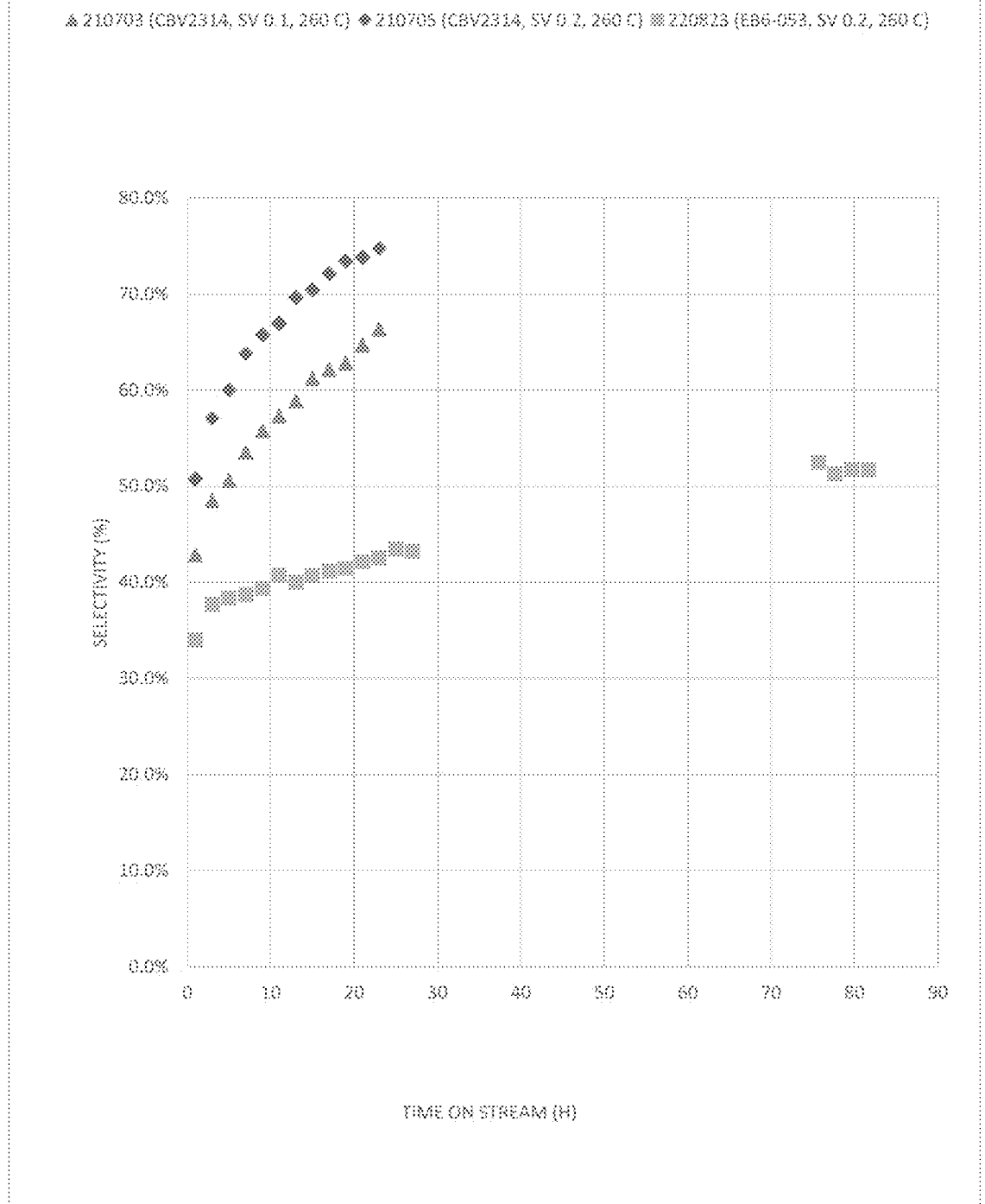
FIG. 3A and FIG. 3B depict time-on-stream selectivity to primary oligomerization products ($C_6$, $C_9$, $C_{12}$, $C_{15}$) and oligomers with carbon number >10 ($C_{10+}$) for CBV2314 and MFI CATALYST 1/EB6-053 using reaction conditions: 260° C., propene partial pressure 165 kPa, space velocities of 0.1 and 0.2 (mol $C_3H_6$) (mol $H^+$)$^{-1}$ s$^{-1}$.
Figure 3B:
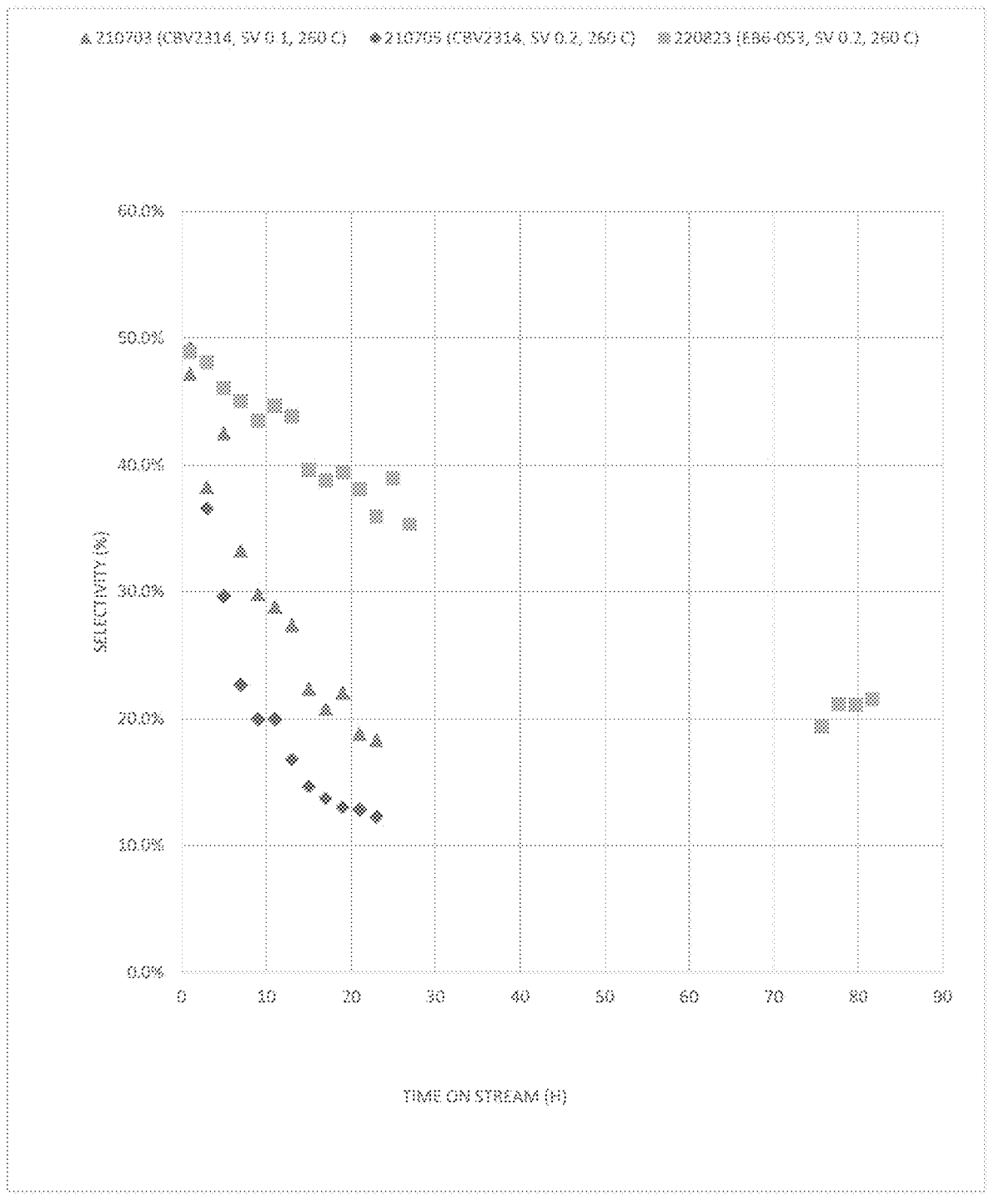

FIG. 2 shows that MFI CATALYST 1/EB6-053 exhibited higher overall conversion at the same reaction conditions (260° C., space velocity (SV)=0.2 (mol C$_3$H$_6$) (mol H$^+$)$^{-1}$ s$^{-1}$), relative to that of CBV2314. CBV2314 showed near iso-conversion with MFI CATALYST 1/EB6-053 at a space velocity half (0.1 (mol C$_3$H$_6$) (mol H$^+$)$^{-1}$ s$^{-1}$) that of MFI CATALYST 1/EB6-053. Deactivation was observed in both catalysts in time-on-stream. However, MFI CATALYST 1/EB6-053 showed stable product distribution as a function of reaction time relative to CBV2314, as depicted in FIG. 3.

MFI CATALYST 1/EB6-053 had significantly lower selectivity to primary oligomerization products (C$_6$, C$_9$, C$_{12}$, C$_{15}$) compared to the commercial CBV2314 catalyst, and the selectivity did not increase as much with time-on-stream compared to CBV2314. MFI CATALYST 1/EB6-053 showed higher selectivity to C$_{10+}$ olefins compared to CBV2314. The initial C$_{10+}$ selectivities were similar for the two catalysts, but MFI CATALYST 1/EB6-053 showed slower decrease in selectivity towards C$_{10+}$ with time-on-stream compared to that of CBV2314. Interestingly, it also appears that the C$_{10+}$ selectivity deactivation tread was more linear for MFI CATALYST 1/EB6-053, rather than the exponential decay observed in CBV2314.

Figure 4A:
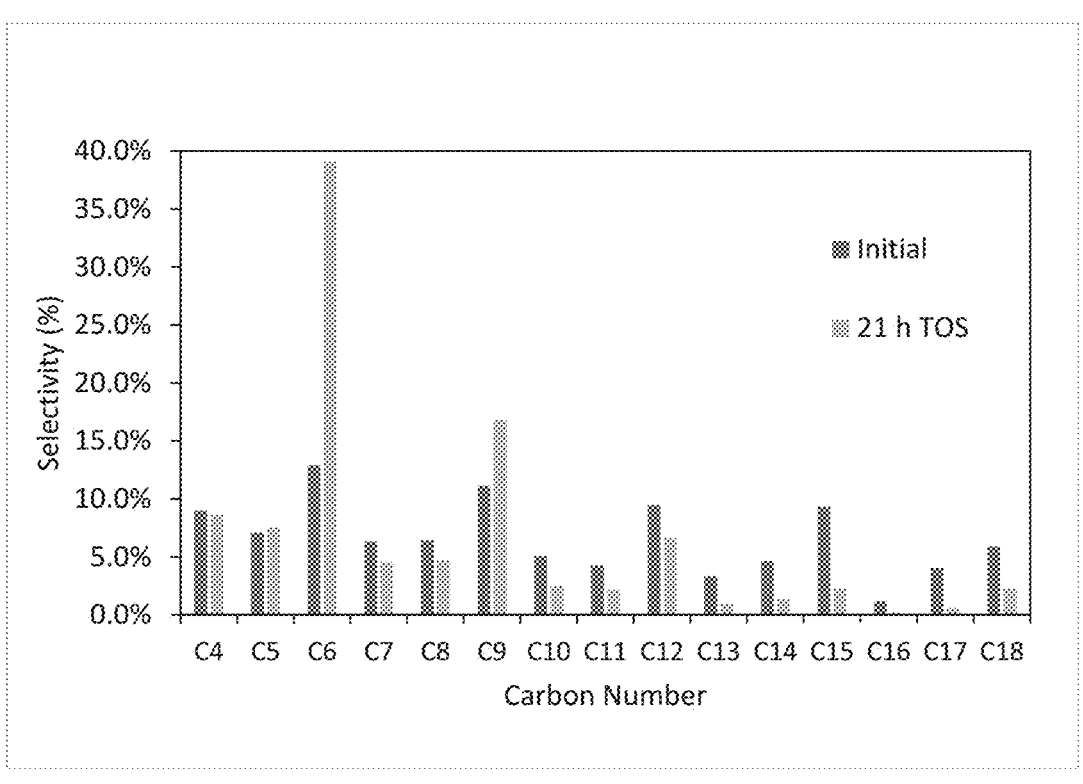
FIG. 4A and FIG. 4B depict product distributions at iso-conversion at initial time-on-stream (1 h) and 21 h time-on-stream for CBV2314 using reaction conditions.
Figure 4B:
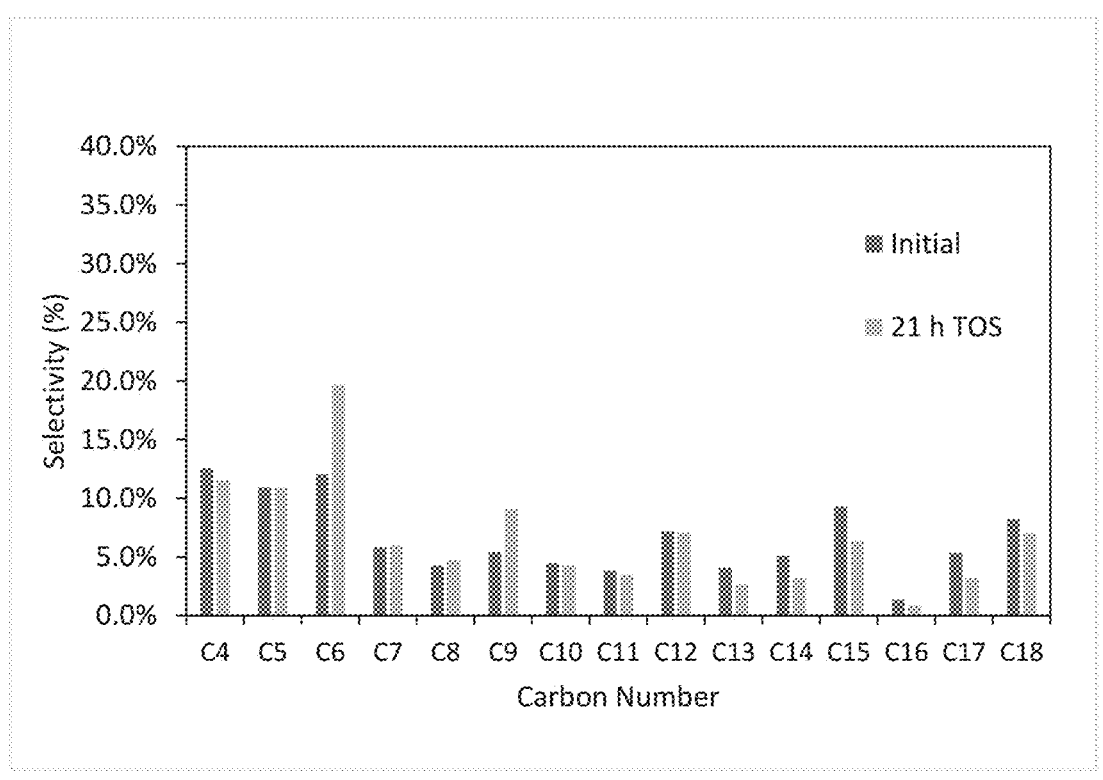

FIG. 4 shows total product distribution at initial time on stream (1 h) and at 21 h time-on-stream for CBV2314 and MFI CATALYST 1/EB6-053 at iso-conversion. This confirms the observation that MFI CATALYST 1/EB6-053 displayed lower selectivity to primary oligomers (and thus greater selectivity to cracking products) compared to CBV2314, and greater selectivity to heavier products ($C_{10+}$). It also showed the change in product distribution from initial to later time on stream was more significant in CBV2314 than in MFI CATALYST 1/EB6-053.

FIG. 5 showed that MFI CATALYST 2/SL1-070 had significantly higher conversion than CBV2314 at the same reaction conditions. In fact, the highest experimental conversion achieved on the CBV2314 sample in any experiment we conducted was still lower than the conversion achieved on MFI CATALYST 2/SL1-070. The deactivation pattern of total conversion appeared similar in both catalysts.

FIG. 6 shows that MFI CATALYST 2/SL1-070 had a very stable product distribution, with very little change in either primary oligomer selectivity or $C_{10+}$ selectivity with time on stream. While initial selectivities were similar for both catalysts, the MFI CATALYST 2/SL1-070 maintained a stable selectivity profile despite the decrease in conversion with time-on-stream. This has significant advantages for developing a continuous process for producing a liquid product from an oligomerization reactor that is intended for use in chemical and fuel markets.

FIG. 7 shows total product distribution at initial time on stream (1 h) and at 21 h time on stream. MFI CATALYST 2/SL1-070 had significantly lower selectivity to primary oligomers and greater selectivity to heavier products ($C_{10+}$) compared to that of CBV2314 (FIG. 4A). It also shows that the product distribution has very little change in MFI CATALYST 2/SL1-070, especially compared to CBV2314 which changes significantly with time-on-stream.

FIG. 8 depicts time-on-stream conversion of propene oligomerization on CBV2314 and MFI CATALYST 2/SL1-070 (reaction condition: 260° C., propene partial pressure 165 kPa, space velocities of 0.1-0.8 (mol $C_3H_6$) (mol $H^+$)$^{-1}$ s$^{-1}$). FIGS. 9A and 9B depicts time-on-stream selectivity to (a) primary oligomerization products ($C_6$, $C_9$, $C_{12}$, $C_{15}$) and (b) oligomers with carbon number >10 ($C_{10+}$) for CBV2314 and MFI CATALYST 2/SL1-070 measured at different space velocities.

CBV2314 yielded near iso-conversion at a space velocity that is approximately 12% lower (0.1 (mol $C_3H_6$) (mol $H^+$)$^{-1}$ s$^{-1}$) than that of MFI CATALYST 2/SL1-070 (0.8 (mol $C_3H_6$) (mol $H^+$)$^{-1}$ s$^{-1}$). The deactivation pattern appeared similar in both catalysts. However, MFI CATALYST 2/SL1-070 showed stable product distribution as a function of reaction time relative to CBV2314 compared at iso-conversion condition, as depicted in FIG. 9.

FIGS. 10A and 10B depict product distributions at initial time-on-stream (1 h) and 21 h time-on-stream of MFI CATALYST 2/SL1-070 at different space velocity of (a) 0.6 (mol $C_3H_6$) (mol $H^+$)$^{-1}$ s$^{-1}$ and (b) 0.8 (mol $C_3H_6$) (mol $H^+$)$^{-1}$ s$^{-1}$ (reaction condition: 260° C., propene partial pressure 165 kPa).

FIG. 7 and FIGS. 10A-10B confirm the observation that as the space velocity decreases, MFI CATALYST 2/SL1-070 displays lower selectivity to primary oligomers (and thus greater selectivity to cracking products), and greater selectivity to heavier products ($C_{10+}$).

FIGS. 11A, 11B, and 11C depict propene oligomerization reaction data measured on MFI CATALYST 2/SL1-070 (reaction condition: 260° C., propene partial pressures of 165 kPa, 602 kPa, 45 kPa, 21 kPa, space velocity of 0.8 (mol $C_3H_6$) (mol $H^+$)$^{-1}$ s$^{-1}$) for the (FIG. 11A) time-on-stream conversion, (FIG. 11B) time-on-stream selectivity to primary oligomerization products ($C_6$, $C_9$, $C_{12}$, $C_{15}$) and (FIG. 11C) time-on-stream selectivity to oligomers with carbon number >10 ($C_{10+}$). FIGS. 11A-11C show that MFI CATALYST 2/SL1-070 had a very stable product distribution, with very little change in either primary oligomer selectivity or $C_{10+}$ selectivity with time on stream, as the reactant pressure was varied. The MFI CATALYST 2/SL1-070 maintained a stable selectivity profile despite the decrease in conversion with time-on-stream, as the reactant pressure was varied. One significant finding is that the primary oligomer selectivity or $C_{10+}$ selectivity achieved different steady-state values at different reactant pressures.

FIGS. 12A-12C show that the product selectivity of MFI CATALYST 2/SL1-070 is tunable with reaction temperature, as different temperatures yielded different steady state selectivity values, particularly in $C_{10+}$ selectivity. In addition, increasing the reaction temperature by 20° C. (from a baseline of 260° C.) yielded significantly higher conversion, with an initial conversion of 88%. Higher temperatures displayed more stable product selectivity with time-one-stream than lower temperatures, with $C_{10+}$ selectivity being essentially the same at initial (1 h) time-on-stream and 27 hours time-on-stream at 270° C. and 280° C.

FIGS. 14A-14C show a comparison between MFI CATALYST 2/SL1-070 and MFI CATALYST 3/SL2-078. These figures show that at identical reaction conditions, MFI CATALYST 3/SL2-078 displays higher conversion and more stable product selectivity with time-on-stream. These figures show that the even smaller crystallite size of MFI CATALYST 3/SL2-078 leads to improved performance while maintaining the desirable properties of MFI CATALYST 2/SL1-070 as discussed previously.

FIGS. 15A-15C show another comparison between MFI CATALYST 2/SL1-070 and MFI CATALYST 3/SL2-078. These figures show that smaller crystallite size catalysts result in improved performance over a range of pressures. One significant finding is that at low partial pressure (45 kPa), MFI CATALYST 3/SL2-078 had higher conversion and that was more stable with time-on-stream. Different reactant pressures also achieved different steady-state values for primary oligomer selectivity and $C_{10+}$ selectivity, but with improved stability.

FIGS. 16A-16C show another comparison between MFI CATALYST 2/SL1-070 and MFI CATALYST 3/SL2-078. These figures show that smaller crystallite size yields improved performance over a range of temperatures. At high temperature (280° C.), MFI CATALYST 3/SL2-078 had more stable and higher conversion, with initial conversion (1 h) of 95% decreasing to only 85% at 27 hours time-on-stream. Change in selectivity with time-on-stream was equal or lower at all temperatures for MFI CATALYST 3/SL2-078.

The above results show that product selectivity from an olefin oligomerization catalyst can be stabilized to be at a near-constant composition over longer times-on-stream, even during catalyst deactivation, via reduction in crystallite sizes of the zeolite catalysts that have been traditionally studied for this chemistry. This catalyst offers significant new advantages for developing a continuous process for producing a liquid product from an oligomerization reactor that is intended for use in chemical and fuel markets. It was surprisingly discovered that a stable oligomerization product distribution could be made by tailoring the catalyst design and properties. It was also discovered that by choosing the right reaction conditions the composition of the product distribution can be systematically changed in a steady-state manner.

Other embodiments provided herein include any one or more of the following numbered paragraphs:

A method for converting alkenes to higher liquid products, comprising: contacting one or more alkenes having 2 to 12 carbon atoms with a MFI zeolite having a silicon to aluminum ratio (Si:Al) of about 10 to about 100 and a crystallite size of about 0.001 μm to about 0.1 μm; and oligomerizing the one or more alkenes in the presence of the MFI zeolite to form an oligomer having 4 to 26 carbon atoms.

2. The method according to paragraph 1, wherein the silicon to aluminum ratio (Si:Al) is about 20 to about 50.

3. The method according to paragraphs 1 and/or 2, wherein the crystallite size is about 0.01 μm to about 0.05 μm.

4. The method according to any paragraph 1 to 4, wherein the one or more alkenes are derived from natural gas, natural gas liquids, or mixtures of both.

5. The method according to any paragraph 1 to 5, wherein the one or more alkenes each have 2 to 6 carbon atoms.

6. The method according to any paragraph 1 to 6, wherein the oligomer contains less than about 5% aromatics and less than about 10 ppm sulfur.

7. The method according to any paragraph 1 to 7, wherein the oligomer has a boiling point in the range of about 170° C. to about 360° C.

8. A method for converting alkenes to higher liquid products, comprising: obtaining one or more alkenes having 2 to 12 carbon atoms from natural gas, natural gas liquids, or mixtures thereof; contacting the one or more alkenes with a MFI zeolite having a silicon to aluminum ratio (Si:Al) of about 20 to about 50 and a crystallite size of about 0.001 μm to about 0.05 μm; and oligomerizing the one or more alkenes in the presence of the MFI zeolite to form an oligomer having 4 to 26 carbon atoms.

9. The method according to paragraph 8, wherein the one or more alkenes each have 4 to 6 carbon atoms.

10. The method according to paragraphs 8 and/or 9, wherein the oligomer contains less than about 5% aromatics and less than about 10 ppm sulfur.

11. The method according to any paragraph 8 to 10, wherein the oligomer has a boiling point in the range of about 170° C. to about 360° C.

12. A method for converting alkenes to higher liquid products, comprising: contacting one or more alkenes having 2 to 12 carbon atoms with a MFI zeolite comprising a silicon to aluminum ratio (Si:Al) of about 10 to about 100 and a crystallite size of about 0.001 μm to about 0.1 μm; oligomerizing the one or more alkenes in the presence of the MFI zeolite to form an oligomer having 4 to 26 carbon atoms, wherein the MFI zeolite is obtained by: combining a source of quaternary ammonium surfactant with hydrocarbon chains, a source of sodium, and water to form an aqueous solution; homogenizing the aqueous solution; adding a source of aluminum to the homogenized aqueous solution to form an intermediate agent; homogenizing the intermediate agent to form an aluminum-containing intermediate agent; adding a source of silicon to the aluminum-containing intermediate agent to form an aluminosilicate-containing intermediate agent; homogenizing the aluminosilicate-containing intermediate agent to form a synthesis gel; and crystallizing the synthesis gel to form the MFI zeolite.

13. The method according to paragraph 12, further comprising conducting an ion-exchange treatment to remove unreacted reagents, and then recovering the acid-form zeolite.

14. The method according to paragraphs 12 and/or 13, wherein the quaternary ammonium surfactants with hydrocarbon chains are represented by: CnH2n+1-N+(CH3)2-C6H12-N+(CH3)2-CnH2n+1, where n is 4 to 8.

15. The method according to any paragraph 12 to 14, wherein the crystallizing the synthesis gel to form the MFI zeolite occurs at a temperature of about 90° C. to about 150° C.

16. The method according to any paragraph 12 to 15, wherein the source of quaternary ammonium surfactant with hydrocarbon chains is tetrapropylammonium hydroxide.

17. The method according to any paragraph 12 to 16, wherein a ratio of the quaternary ammonium surfactant with hydrocarbon chains to silicon is 0.05 to 0.20.

18. The method according to any paragraph 12 to 17, wherein the source of silicon is colloidal silica, a silicon alkoxide compound, fumed silica, amorphous silica, aluminosilicate, or any combinations thereof.

19. The method according to any paragraph 12 to 18, wherein the source of aluminum is aluminum hydroxide, aluminum sulfate, aluminum nitrate, aluminosilicate, or derivatives thereof.

20. The method according to any paragraph 12 to 19, wherein the source of the one or more alkenes having 2 to 12 carbon atoms is from natural gas, natural gas liquids, or mixtures thereof.

In the above detailed description, the specific embodiments of this disclosure have been described in connection with its preferred embodiments. However, to the extent that the above description is specific to a particular embodiment or a particular use of this disclosure, this is intended to be illustrative only and merely provides a concise description of the exemplary embodiments. Accordingly, the disclosure is not limited to the specific embodiments described above, but rather, the disclosure includes all alternatives, modifications, and equivalents falling within the true scope of the appended claims. Various modifications and variations of this disclosure will be obvious to a worker skilled in the art and it is to be understood that such modifications and variations are to be included within the purview of this application and the spirit and scope of the claims.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, meaning the values take into account experimental error, machine tolerances and other variations that would be expected by a person having ordinary skill in the art.

The foregoing has also outlined features of several embodiments so that those skilled in the art can better understand the present disclosure. Those skilled in the art should appreciate that they can readily use the present disclosure as a basis for designing or modifying other methods or devices for carrying out the same purposes and/or achieving the same advantages of the embodiments disclosed herein. Those skilled in the art should also realize that such equivalent constructions do not depart from the spirit and scope of the present disclosure, and that they can make various changes, substitutions, and alterations herein without departing from the spirit and scope of the present disclosure, and the scope thereof is determined by the claims that follow.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for converting alkenes to higher liquid products, comprising:

combining a source of quaternary ammonium surfactant with hydrocarbon chains, a source of sodium, and water to form an aqueous solution, wherein the source of the quaternary ammonium surfactant with hydrocarbon chains is represented by: $C_nH_{2n+1}$—$N^+(CH_3)_2$—$C_6H_{12}$—$N^+(CH_3)_2$—$C_nH_{2n+1}$, where n is 4 to 8;

homogenizing the aqueous solution;

adding a source of aluminum to the homogenized aqueous solution to form an intermediate agent;

homogenizing the intermediate agent to form an aluminum-containing intermediate agent;

adding a source of silicon to the aluminum-containing intermediate agent to form an aluminosilicate-containing intermediate agent;

homogenizing the aluminosilicate-containing intermediate agent to form a synthesis gel;

crystallizing the synthesis gel to form a MFI zeolite;

contacting one or more alkenes having 2 to 12 carbon atoms with the MFI zeolite comprising a silicon to aluminum ratio (Si:Al) of about 10 to about 100 and a crystallite size of about 0.001 μm to about 0.1 μm; and oligomerizing the one or more alkenes in the presence of the MFI zeolite to form an oligomer having 4 to 26 carbon atoms.

2. The method of claim 1, further comprising conducting an ion-exchange treatment to remove unreacted reagents, and then recovering the acid-form zeolite.

3. The method of claim 1, wherein the quaternary ammonium surfactants with hydrocarbon chains are represented by: $C_nH_{2n+1}$—$N^+(CH_3)_2$—$C_6H_{12}$—$N^+(CH_3)_2$—$C_nH_{2n+1}$, where n is 4 to 8.

4. The method of claim 1, wherein the crystallizing the synthesis gel to form the MFI zeolite occurs at a temperature of about 90° C. to about 150° C.

5. The method of claim 1, wherein the source of quaternary ammonium surfactant with hydrocarbon chains is tetrapropylammonium hydroxide.

6. The method of claim 1, wherein a ratio of the quaternary ammonium surfactant with hydrocarbon chains to silicon is 0.05 to 0.20 and a ratio of Na:Al is 0.1 to 0.3.

7. The method of claim 1, wherein the source of silicon is colloidal silica, a silicon alkoxide compound, fumed silica, amorphous silica, aluminosilicate, or any combinations thereof.

8. The method of claim 1, wherein the source of aluminum is aluminum hydroxide, aluminum sulfate, aluminum nitrate, aluminosilicate, or derivatives thereof.

9. The method of claim 1, wherein the source of the one or more alkenes having 2 to 12 carbon atoms is from natural gas, natural gas liquids, or mixtures thereof.

10. A method for converting alkenes to higher liquid products, comprising:

combining a source of quaternary ammonium surfactant with hydrocarbon chains, a source of sodium, and water to form an aqueous solution, wherein the source of the quaternary ammonium surfactant with hydrocarbon chains is represented by: $C_nH_{2n+1}$—$N^+(CH_3)_2$—$C_6H_{12}$—$N^+(CH_3)_2$—$C_nH_{2n+1}$, where n is 4 to 8;

homogenizing the aqueous solution;

adding a source of aluminum to the homogenized aqueous solution to form an intermediate agent;

homogenizing the intermediate agent to form an aluminum-containing intermediate agent;

adding a source of silicon to the aluminum-containing intermediate agent to form an aluminosilicate-containing intermediate agent, wherein a ratio of the quaternary ammonium surfactant with hydrocarbon chains to silicon is 0.05 to 0.20;

homogenizing the aluminosilicate-containing intermediate agent to form a synthesis gel;

crystallizing the synthesis gel to form a MFI zeolite;

contacting one or more alkenes having 2 to 12 carbon atoms with the MFI zeolite comprising a silicon to aluminum ratio (Si:Al) of about 10 to about 100 and a crystallite size of about 0.001 μm to about 0.1 μm; and oligomerizing the one or more alkenes in the presence of the MFI zeolite to form an oligomer having 4 to 26 carbon atoms.

11. The method of claim 10, wherein the silicon to aluminum ratio (Si:Al) is about 20 to about 50.

12. The method of claim 10, wherein the crystallite size is about 0.01 μm to about 0.05 μm.

13. The method of claim 10, wherein the one or more alkenes are derived from natural gas, natural gas liquids, or mixtures of both.

14. The method of claim 10, wherein the one or more alkenes each have 2 to 6 carbon atoms.

15. The method of claim 10, wherein the oligomer contains less than about 5% aromatics and less than about 10 ppm sulfur.

16. The method of claim 10, wherein the oligomer has a boiling point in the range of about 170° C. to about 360° C.

17. The method of claim 10, wherein the oligomer contains less than about 5% aromatics and less than about 10 ppm sulfur, and the oligomer has a boiling point in the range of about 170° C. to about 360° C.

* * * * *